US008329866B2

(12) United States Patent
Rosendahl et al.

(10) Patent No.: US 8,329,866 B2
(45) Date of Patent: Dec. 11, 2012

(54) LONG ACTING VEGF INHIBITORS AND METHODS OF USE

(75) Inventors: Mary S. Rosendahl, Broomfield, CO (US); George N. Cox, III, Louisville, CO (US)

(73) Assignee: Bolder Biotechnology, Inc., Boulder, CO (US)

( * ) Notice: Subject to any disclaimer, the term of this patent is extended or adjusted under 35 U.S.C. 154(b) by 1005 days.

(21) Appl. No.: 12/089,042

(22) PCT Filed: Oct. 3, 2006

(86) PCT No.: PCT/US2006/038727
§ 371 (c)(1), (2), (4) Date: Nov. 10, 2008

(87) PCT Pub. No.: WO2007/041614
PCT Pub. Date: Apr. 12, 2007

(65) Prior Publication Data

US 2009/0163411 A1 Jun. 25, 2009

Related U.S. Application Data

(60) Provisional application No. 60/723,354, filed on Oct. 3, 2005.

(51) Int. Cl.
*C07K 5/00* (2006.01)
*A61K 38/00* (2006.01)

(52) U.S. Cl. ....................................... 530/350; 514/13.3

(58) Field of Classification Search ........................ None
See application file for complete search history.

(56) References Cited

U.S. PATENT DOCUMENTS

| | | | |
|---|---|---|---|
| 4,588,585 | A | 5/1986 | Mark et al. |
| 5,166,322 | A | 11/1992 | Shaw et al. |
| 5,206,344 | A | 4/1993 | Katre et al. |
| 5,208,158 | A | 5/1993 | Bech et al. |
| 5,766,897 | A | 6/1998 | Braxton |
| 5,849,535 | A | 12/1998 | Cunningham et al. |
| 7,070,959 | B1 | 7/2006 | Papadopoulos |
| 7,087,411 | B2 | 8/2006 | Daly et al. |
| 7,279,159 | B2 | 10/2007 | Daly et al. |
| 7,303,747 | B2 | 12/2007 | Wiegand et al. |
| 7,306,799 | B2 | 12/2007 | Wiegand et al. |
| 7,396,664 | B2 | 7/2008 | Daly et al. |
| 7,399,612 | B2 | 7/2008 | Daly et al. |
| 2009/0062200 | A1 | 3/2009 | Daly et al. |

FOREIGN PATENT DOCUMENTS

| | | |
|---|---|---|
| EP | 0355460 | 2/1990 |
| EP | 0458064 | 11/1991 |
| WO | 90/12874 | 11/1990 |
| WO | 93/00109 | 1/1993 |
| WO | 94/12219 | 6/1994 |
| WO | 94/22466 | 10/1994 |
| WO | 95/11987 | 5/1995 |
| WO | 95/32003 | 11/1995 |
| WO | 96/31537 | 10/1996 |

OTHER PUBLICATIONS

EyeTech Study Group. 2002. Preclinical and phase 1A clinical evaluation of an anti-VEGF pegylated aptamer (EYE001) for the treatment of exudative age-related macular degeneration. Retina 22:143-152.*
Wu, et al, "Rat soluble form Flt-1" 1999, Accession No. Q9JJ08.*
Gene Result, Accession No. Q9jj08, p. 4. Accessed Jul. 10, 2011 at: http://www.ncbi.nlm.nih.gov/gene?term=Q9JJ08.*
Yamaguchi, 2002, Soluble Flt-1 (Soluble VEGFR-1), a Potent Natural Antiangiogenic Molecule in Mammals, Is Phylogenetically Conserved in Avians. Biochemical and Biophysical Research Communications 291, 554-559.*
Bazan et al., Science, vol. 257 No. 5068, pp. 410-413 (Jul. 1992).
Bazan, Immunology Today, 11:350-354 (1990).
Bowie et al., Science, vol. 247 No. 4948, pp. 1306-1310 (Mar. 1990).
Campbell et al., J. Peptide Res., 49:527-537 (1997).
Cunningham BC, Wells JA. Science. 244:1081-5, (1989).
Cunningham et al., Science, 243:1330-1336 (1989).
Goodson and Katre, Bio/Technology, 8:343-346 (1990).
Mott and Campbell, Curr Opin Struct Biol, 5:114-121 (1995).
Olins P.O. et al: 'Saturation muatgenesis of human interleukin-3' Journal of Biological Chemistry vol. 270, No. 40, Oct. 6, 1996, pp. 23754-23760.
Sprang and Bazan, Curr. Opin. Struct. Biol., 3:815-827 (1993).
Wells, Ann. Rev. Biochem., 65:609-634 (1996).
Zalipsky, Adv. Drug Delivery Reviews, 16:157-182 (1995).
Zurawaki et al. "Definition and spatial location of mouse interleukin-2 residues that interact with the heterotrmeric receptor", Embo Journal 12, 5113-5119, 1993.
International Preliminary Examination Report for International (PCT) Patent Application No. PCT/US98/14497, mailed May 11, 1999.
International Search Report for International (PCT) Patent Application No. PCT/US98/14497, mailed Oct. 22, 1998.

(Continued)

*Primary Examiner* — Jeffrey Stucker
*Assistant Examiner* — Sandra Wegert
(74) *Attorney, Agent, or Firm* — Sheridan Ross P.C.

(57) ABSTRACT

Disclosed are polymer sFlt-1 conjugates, variants of sFlt-1, compositions comprising such conjugates and variants, including cysteine variants of sFlt-1. Also disclosed is the use of such conjugates, variants and compositions in methods to inhibit the activity of VEGF, to inhibit angiogenesis, and to treat or reduce at least one symptom of diseases and conditions in which it is desirable to inhibit VEGF activity and/or angiogenesis.

11 Claims, No Drawings

OTHER PUBLICATIONS

International Search Report and Written Opinion for International (PCT) Application No. PCT/US06/38727, mailed Apr. 8, 2008, pp. 10.

Maynard, et al., "Excess placental soluble fms-like tyrosine kinase 1 (sFlt 1) may contribute to endothelial dysfunction, hypertension, and proteinuria in preeclampsia", The Journal of Clinical Investigation, Mar. 2003, vol. III, No. 5, pp. 649-658.

Holash et al. "VEGF-Trap: a VEGF blocker with potent antitumor effects.", Proc Natl Acad Sci U S A. Aug. 20, 2002;99(17):11393-8. Epub Aug. 12, 2002.

* cited by examiner

SEQUENCE LISTING

<160> NUMBER OF SEQ ID NOS: 34

<210> SEQ ID NO 1
<211> LENGTH: 2651
<212> TYPE: DNA
<213> ORGANISM: Homo sapiens
<220> FEATURE:

```
<221> NAME/KEY: CDS
<222> LOCATION: (250)..(2313)

<400> SEQUENCE: 1

gcggacactc ctctcggctc ctccccggca gcggcggcgg ctcggagcgg gctccggggc      60

tcgggtgcag cggccagcgg gcctggcggc gaggattacc cggggaagtg gttgtctcct     120

ggctggagcc gcgagacggg cgctcagggc gcggggccgg cggcggcgaa cgagaggacg     180

gactctggcg gccgggtcgt tggccggggg agcgcgggca ccgggcgagc aggccgcgtc     240

gcgctcacc atg gtc agc tac tgg gac acc ggg gtc ctg ctg tgc gcg ctg     291
          Met Val Ser Tyr Trp Asp Thr Gly Val Leu Leu Cys Ala Leu
          1               5                   10

ctc agc tgt ctg ctt ctc aca gga tct agt tca ggt tca aaa tta aaa       339
Leu Ser Cys Leu Leu Leu Thr Gly Ser Ser Ser Gly Ser Lys Leu Lys
15                  20                  25                  30

gat cct gaa ctg agt tta aaa ggc acc cag cac atc atg caa gca ggc       387
Asp Pro Glu Leu Ser Leu Lys Gly Thr Gln His Ile Met Gln Ala Gly
                35                  40                  45

cag aca ctg cat ctc caa tgc agg ggg gaa gca gcc cat aaa tgg tct       435
Gln Thr Leu His Leu Gln Cys Arg Gly Glu Ala Ala His Lys Trp Ser
            50                  55                  60

ttg cct gaa atg gtg agt aag gaa agc gaa agg ctg agc ata act aaa       483
Leu Pro Glu Met Val Ser Lys Glu Ser Glu Arg Leu Ser Ile Thr Lys
        65                  70                  75

tct gcc tgt gga aga aat ggc aaa caa ttc tgc agt act tta acc ttg       531
Ser Ala Cys Gly Arg Asn Gly Lys Gln Phe Cys Ser Thr Leu Thr Leu
    80                  85                  90

aac aca gct caa gca aac cac act ggc ttc tac agc tgc aaa tat cta       579
Asn Thr Ala Gln Ala Asn His Thr Gly Phe Tyr Ser Cys Lys Tyr Leu
95                  100                 105                 110

gct gta cct act tca aag aag aag gaa aca gaa tct gca atc tat ata       627
Ala Val Pro Thr Ser Lys Lys Lys Glu Thr Glu Ser Ala Ile Tyr Ile
                115                 120                 125

ttt att agt gat aca ggt aga cct ttc gta gag atg tac agt gaa atc       675
Phe Ile Ser Asp Thr Gly Arg Pro Phe Val Glu Met Tyr Ser Glu Ile
            130                 135                 140

ccc gaa att ata cac atg act gaa gga agg gag ctc gtc att ccc tgc       723
Pro Glu Ile Ile His Met Thr Glu Gly Arg Glu Leu Val Ile Pro Cys
        145                 150                 155

cgg gtt acg tca cct aac atc act gtt act tta aaa aag ttt cca ctt       771
Arg Val Thr Ser Pro Asn Ile Thr Val Thr Leu Lys Lys Phe Pro Leu
    160                 165                 170

gac act ttg atc cct gat gga aaa cgc ata atc tgg gac agt aga aag       819
Asp Thr Leu Ile Pro Asp Gly Lys Arg Ile Ile Trp Asp Ser Arg Lys
175                 180                 185                 190

ggc ttc atc ata tca aat gca acg tac aaa gaa ata ggg ctt ctg acc       867
Gly Phe Ile Ile Ser Asn Ala Thr Tyr Lys Glu Ile Gly Leu Leu Thr
                195                 200                 205

tgt gaa gca aca gtc aat ggg cat ttg tat aag aca aac tat ctc aca       915
Cys Glu Ala Thr Val Asn Gly His Leu Tyr Lys Thr Asn Tyr Leu Thr
            210                 215                 220

cat cga caa acc aat aca atc ata gat gtc caa ata agc aca cca cgc       963
His Arg Gln Thr Asn Thr Ile Ile Asp Val Gln Ile Ser Thr Pro Arg
        225                 230                 235

cca gtc aaa tta ctt aga ggc cat act ctt gtc ctc aat tgt act gct      1011
Pro Val Lys Leu Leu Arg Gly His Thr Leu Val Leu Asn Cys Thr Ala
    240                 245                 250

acc act ccc ttg aac acg aga gtt caa atg acc tgg agt tac cct gat      1059
Thr Thr Pro Leu Asn Thr Arg Val Gln Met Thr Trp Ser Tyr Pro Asp
255                 260                 265                 270
```

```
gaa aaa aat aag aga gct tcc gta agg cga cga att gac caa agc aat     1107
Glu Lys Asn Lys Arg Ala Ser Val Arg Arg Arg Ile Asp Gln Ser Asn
                275                 280                 285

tcc cat gcc aac ata ttc tac agt gtt ctt act att gac aaa atg cag     1155
Ser His Ala Asn Ile Phe Tyr Ser Val Leu Thr Ile Asp Lys Met Gln
            290                 295                 300

aac aaa gac aaa gga ctt tat act tgt cgt gta agg agt gga cca tca     1203
Asn Lys Asp Lys Gly Leu Tyr Thr Cys Arg Val Arg Ser Gly Pro Ser
        305                 310                 315

ttc aaa tct gtt aac acc tca gtg cat ata tat gat aaa gca ttc atc     1251
Phe Lys Ser Val Asn Thr Ser Val His Ile Tyr Asp Lys Ala Phe Ile
    320                 325                 330

act gtg aaa cat cga aaa cag cag gtg ctt gaa acc gta gct ggc aag     1299
Thr Val Lys His Arg Lys Gln Gln Val Leu Glu Thr Val Ala Gly Lys
335                 340                 345                 350

cgg tct tac cgg ctc tct atg aaa gtg aag gca ttt ccc tcg ccg gaa     1347
Arg Ser Tyr Arg Leu Ser Met Lys Val Lys Ala Phe Pro Ser Pro Glu
                355                 360                 365

gtt gta tgg tta aaa gat ggg tta cct gcg act gag aaa tct gct cgc     1395
Val Val Trp Leu Lys Asp Gly Leu Pro Ala Thr Glu Lys Ser Ala Arg
            370                 375                 380

tat ttg act cgt ggc tac tcg tta att atc aag gac gta act gaa gag     1443
Tyr Leu Thr Arg Gly Tyr Ser Leu Ile Ile Lys Asp Val Thr Glu Glu
        385                 390                 395

gat gca ggg aat tat aca atc ttg ctg agc ata aaa cag tca aat gtg     1491
Asp Ala Gly Asn Tyr Thr Ile Leu Leu Ser Ile Lys Gln Ser Asn Val
    400                 405                 410

ttt aaa aac ctc act gcc act cta att gtc aat gtg aaa ccc cag att     1539
Phe Lys Asn Leu Thr Ala Thr Leu Ile Val Asn Val Lys Pro Gln Ile
415                 420                 425                 430

tac gaa aag gcc gtg tca tcg ttt cca gac ccg gct ctc tac cca ctg     1587
Tyr Glu Lys Ala Val Ser Ser Phe Pro Asp Pro Ala Leu Tyr Pro Leu
                435                 440                 445

ggc agc aga caa atc ctg act tgt acc gca tat ggt atc cct caa cct     1635
Gly Ser Arg Gln Ile Leu Thr Cys Thr Ala Tyr Gly Ile Pro Gln Pro
            450                 455                 460

aca atc aag tgg ttc tgg cac ccc tgt aac cat aat cat tcc gaa gca     1683
Thr Ile Lys Trp Phe Trp His Pro Cys Asn His Asn His Ser Glu Ala
        465                 470                 475

agg tgt gac ttt tgt tcc aat aat gaa gag tcc ttt atc ctg gat gct     1731
Arg Cys Asp Phe Cys Ser Asn Asn Glu Glu Ser Phe Ile Leu Asp Ala
    480                 485                 490

gac agc aac atg gga aac aga att gag agc atc act cag cgc atg gca     1779
Asp Ser Asn Met Gly Asn Arg Ile Glu Ser Ile Thr Gln Arg Met Ala
495                 500                 505                 510

ata ata gaa gga aag aat aag atg gct agc acc ttg gtt gtg gct gac     1827
Ile Ile Glu Gly Lys Asn Lys Met Ala Ser Thr Leu Val Val Ala Asp
                515                 520                 525

tct aga att tct gga atc tac att tgc ata gct tcc aat aaa gtt ggg     1875
Ser Arg Ile Ser Gly Ile Tyr Ile Cys Ile Ala Ser Asn Lys Val Gly
            530                 535                 540

act gtg gga aga aac ata agc ttt tat atc aca gat gtg cca aat ggg     1923
Thr Val Gly Arg Asn Ile Ser Phe Tyr Ile Thr Asp Val Pro Asn Gly
        545                 550                 555

ttt cat gtt aac ttg gaa aaa atg ccg acg gaa gga gag gac ctg aaa     1971
Phe His Val Asn Leu Glu Lys Met Pro Thr Glu Gly Glu Asp Leu Lys
    560                 565                 570

ctg tct tgc aca gtt aac aag ttc tta tac aga gac gtt act tgg att     2019
Leu Ser Cys Thr Val Asn Lys Phe Leu Tyr Arg Asp Val Thr Trp Ile
575                 580                 585                 590
```

```
tta ctg cgg aca gtt aat aac aga aca atg cac tac agt att agc aag     2067
Leu Leu Arg Thr Val Asn Asn Arg Thr Met His Tyr Ser Ile Ser Lys
                595                 600                 605

caa aaa atg gcc atc act aag gag cac tcc atc act ctt aat ctt acc     2115
Gln Lys Met Ala Ile Thr Lys Glu His Ser Ile Thr Leu Asn Leu Thr
            610                 615                 620

atc atg aat gtt tcc ctg caa gat tca ggc acc tat gcc tgc aga gcc     2163
Ile Met Asn Val Ser Leu Gln Asp Ser Gly Thr Tyr Ala Cys Arg Ala
        625                 630                 635

agg aat gta tac aca ggg gaa gaa atc ctc cag aag aaa gaa att aca     2211
Arg Asn Val Tyr Thr Gly Glu Glu Ile Leu Gln Lys Lys Glu Ile Thr
    640                 645                 650

atc aga ggt gag cac tgc aac aaa aag gct gtt ttc tct cgg atc tcc     2259
Ile Arg Gly Glu His Cys Asn Lys Lys Ala Val Phe Ser Arg Ile Ser
655                 660                 665                 670

aaa ttt aaa agc aca agg aat gat tgt acc aca caa agt aat gta aaa     2307
Lys Phe Lys Ser Thr Arg Asn Asp Cys Thr Thr Gln Ser Asn Val Lys
                675                 680                 685

cat taa aggactcatt aaaaagtaac agttgtctca tatcatcttg atttattgtc      2363
His

actgttgcta actttcaggc tcggaggaga tgctcctccc aaaatgagtt cggagatgat   2423

agcagtaata atgagacccc cgggctccag ctctgggccc cccattcagg ccgagggggc   2483

tgctccgggg ggccgacttg gtgcacgttt ggatttggag gatccctgca ctgccttctc   2543

tgtgtttgtt gctcttgctg ttttctcctg cctgataaac aacaacttgg gatgatcctt   2603

tccattttga tgccaacctc tttttatttt taagcggcgc cctatagt                2651


<210> SEQ ID NO 2
<211> LENGTH: 687
<212> TYPE: PRT
<213> ORGANISM: Homo sapiens

<400> SEQUENCE: 2

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
```

-continued

```
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605
```

```
Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Gly Glu His Cys Asn Lys Lys Ala Val Phe Ser Arg Ile Ser Lys Phe
            660                 665                 670

Lys Ser Thr Arg Asn Asp Cys Thr Thr Gln Ser Asn Val Lys His
        675                 680                 685


<210> SEQ ID NO 3
<211> LENGTH: 21
<212> TYPE: DNA
<213> ORGANISM: Artificial
<220> FEATURE:
<223> OTHER INFORMATION: primer

<400> SEQUENCE: 3

ctatgcggca tcagagcaga t                                              21


<210> SEQ ID NO 4
<211> LENGTH: 22
<212> TYPE: DNA
<213> ORGANISM: Artificial
<220> FEATURE:
<223> OTHER INFORMATION: primer

<400> SEQUENCE: 4

tgtggaattg tgagcggata ac                                             22


<210> SEQ ID NO 5
<211> LENGTH: 21
<212> TYPE: DNA
<213> ORGANISM: Artificial
<220> FEATURE:
<223> OTHER INFORMATION: primer

<400> SEQUENCE: 5

tgctgcaagg cgattaagtt g                                              21


<210> SEQ ID NO 6
<211> LENGTH: 38
<212> TYPE: DNA
<213> ORGANISM: Artificial
<220> FEATURE:
<223> OTHER INFORMATION: primer

<400> SEQUENCE: 6

cgcggatcct ctagttcagg ttcaaaatta aaagatcc                            38


<210> SEQ ID NO 7
<211> LENGTH: 36
<212> TYPE: DNA
<213> ORGANISM: Artificial
<220> FEATURE:
<223> OTHER INFORMATION: primer

<400> SEQUENCE: 7

ccggaattct tatctgattg taatttcttt cttctg                              36


<210> SEQ ID NO 8
<211> LENGTH: 39
<212> TYPE: DNA
<213> ORGANISM: Artificial
```

<220> FEATURE:
<223> OTHER INFORMATION: primer

<400> SEQUENCE: 8
ccggaattct taatgtttca cagtgatgaa tgctttatc 39

<210> SEQ ID NO 9
<211> LENGTH: 28
<212> TYPE: DNA
<213> ORGANISM: Artificial
<220> FEATURE:
<223> OTHER INFORMATION: primer

<400> SEQUENCE: 9
gtgctcacct ctgattgtaa tttctttc 28

<210> SEQ ID NO 10
<211> LENGTH: 21
<212> TYPE: DNA
<213> ORGANISM: Artificial
<220> FEATURE:
<223> OTHER INFORMATION: primer

<400> SEQUENCE: 10
ccacttgaca ctttgatccc t 21

<210> SEQ ID NO 11
<211> LENGTH: 21
<212> TYPE: DNA
<213> ORGANISM: Artificial
<220> FEATURE:
<223> OTHER INFORMATION: primer

<400> SEQUENCE: 11
attggtttgt cgatgtgtga g 21

<210> SEQ ID NO 12
<211> LENGTH: 25
<212> TYPE: DNA
<213> ORGANISM: Artificial
<220> FEATURE:
<223> OTHER INFORMATION: primer

<400> SEQUENCE: 12
ttcaaatctg ttaacacctc agtgc 25

<210> SEQ ID NO 13
<211> LENGTH: 42
<212> TYPE: DNA
<213> ORGANISM: Artificial
<220> FEATURE:
<223> OTHER INFORMATION: primer

<400> SEQUENCE: 13
gaggatgatt aaatgtctag ttcaggttca aaactgaaag at 42

<210> SEQ ID NO 14
<211> LENGTH: 60
<212> TYPE: DNA
<213> ORGANISM: Artificial
<220> FEATURE:
<223> OTHER INFORMATION: primer

<400> SEQUENCE: 14
gatgtgctgg gtacctttta agctcagttc aggatctttc agttttgaac ctgaactaga 60

<210> SEQ ID NO 15
<211> LENGTH: 54
<212> TYPE: DNA
<213> ORGANISM: Artificial
<220> FEATURE:
<223> OTHER INFORMATION: primer

<400> SEQUENCE: 15
ggtacccagc acatcatgca agcaggccag acactgcatc tccaatgccg tggg 54

<210> SEQ ID NO 16
<211> LENGTH: 54
<212> TYPE: DNA
<213> ORGANISM: Artificial
<220> FEATURE:
<223> OTHER INFORMATION: primer

<400> SEQUENCE: 16
caccatttca ggcaaagacc atttatgggc tgcttcccca cggcattgga gatg 54

<210> SEQ ID NO 17
<211> LENGTH: 56
<212> TYPE: DNA
<213> ORGANISM: Artificial
<220> FEATURE:
<223> OTHER INFORMATION: primer

<400> SEQUENCE: 17
ctttgcctga aatggtgagt aaggaaagcg aacgtctgag catcactaaa tctgcc 56

<210> SEQ ID NO 18
<211> LENGTH: 57
<212> TYPE: DNA
<213> ORGANISM: Artificial
<220> FEATURE:
<223> OTHER INFORMATION: primer

<400> SEQUENCE: 18
taaagtactg cagaattgtt tgccattacg accacaggca gatttagtga tgctcag 57

<210> SEQ ID NO 19
<211> LENGTH: 32
<212> TYPE: DNA
<213> ORGANISM: Artificial
<220> FEATURE:
<223> OTHER INFORMATION: primer

<400> SEQUENCE: 19
gcgaattcta aagtactgca gaattgtttg cc 32

<210> SEQ ID NO 20
<211> LENGTH: 51
<212> TYPE: DNA
<213> ORGANISM: Artificial
<220> FEATURE:
<223> OTHER INFORMATION: primer

<400> SEQUENCE: 20
cgcggatcca tcttggagga tgattaaatg tctagttcag gttcaaaact g 51

<210> SEQ ID NO 21
<211> LENGTH: 56
<212> TYPE: DNA
<213> ORGANISM: Artificial
<220> FEATURE:
<223> OTHER INFORMATION: primer

<400> SEQUENCE: 21
cgcggatcca tcttggagga tgattaaatg tctaaactga aagatcctga actgag 56

<210> SEQ ID NO 22
<211> LENGTH: 35
<212> TYPE: DNA
<213> ORGANISM: Artificial
<220> FEATURE:
<223> OTHER INFORMATION: primer

<400> SEQUENCE: 22
cgccatatgt ctaaactgaa agatcctgaa ctgag 35

<210> SEQ ID NO 23
<211> LENGTH: 49
<212> TYPE: DNA
<213> ORGANISM: Artificial
<220> FEATURE:
<223> OTHER INFORMATION: primer

<400> SEQUENCE: 23
cgcggatcca tcttggagga tgattaaatg tgttctaaac tgaaagatc 49

<210> SEQ ID NO 24
<211> LENGTH: 31
<212> TYPE: DNA
<213> ORGANISM: Artificial
<220> FEATURE:
<223> OTHER INFORMATION: primer

<400> SEQUENCE: 24
gaacacagcc caagcatgcc acactggctt c 31

<210> SEQ ID NO 25
<211> LENGTH: 31
<212> TYPE: DNA
<213> ORGANISM: Artificial
<220> FEATURE:
<223> OTHER INFORMATION: primer

<400> SEQUENCE: 25
gaagccagtg tggcatgctt gggctgtgtt c 31

<210> SEQ ID NO 26
<211> LENGTH: 33
<212> TYPE: DNA
<213> ORGANISM: Artificial
<220> FEATURE:
<223> OTHER INFORMATION: primer

<400> SEQUENCE: 26
ggttacgtcg ccatgcatca ctgttacttt aaa 33

<210> SEQ ID NO 27
<211> LENGTH: 33
<212> TYPE: DNA
<213> ORGANISM: Artificial
<220> FEATURE:
<223> OTHER INFORMATION: primer

<400> SEQUENCE: 27
tttaaagtaa cagtgatgca tggcgacgta acc 33

<210> SEQ ID NO 28
<211> LENGTH: 32
<212> TYPE: DNA
<213> ORGANISM: Artificial

<220> FEATURE:
<223> OTHER INFORMATION: primer

<400> SEQUENCE: 28
ggcttcatca tatcatgcgc aacgtacaaa ga 32

<210> SEQ ID NO 29
<211> LENGTH: 32
<212> TYPE: DNA
<213> ORGANISM: Artificial
<220> FEATURE:
<223> OTHER INFORMATION: primer

<400> SEQUENCE: 29
tctttgtacg ttgcgcatga tatgatgaag cc 32

<210> SEQ ID NO 30
<211> LENGTH: 30
<212> TYPE: DNA
<213> ORGANISM: Artificial
<220> FEATURE:
<223> OTHER INFORMATION: primer

<400> SEQUENCE: 30
tcattcaaat ctgtttgcac ctcagtgcat 30

<210> SEQ ID NO 31
<211> LENGTH: 30
<212> TYPE: DNA
<213> ORGANISM: Artificial
<220> FEATURE:
<223> OTHER INFORMATION: primer

<400> SEQUENCE: 31
atgcactgag gtgcaaacag atttgaatga 30

<210> SEQ ID NO 32
<211> LENGTH: 33
<212> TYPE: DNA
<213> ORGANISM: Artificial
<220> FEATURE:
<223> OTHER INFORMATION: primer

<400> SEQUENCE: 32
cgcgaattct tagcatttca cagtgatgaa tgc 33

<210> SEQ ID NO 33
<211> LENGTH: 44
<212> TYPE: DNA
<213> ORGANISM: Artificial
<220> FEATURE:
<223> OTHER INFORMATION: primer

<400> SEQUENCE: 33
gattaaatgt ctaaactgaa atgtccggaa ctgagcttaa aagg 44

<210> SEQ ID NO 34
<211> LENGTH: 44
<212> TYPE: DNA
<213> ORGANISM: Artificial
<220> FEATURE:
<223> OTHER INFORMATION: primer

<400> SEQUENCE: 34
ccttttaagc tcagttccgg acatttcagt ttagacattt aatc 44

LONG ACTING VEGF INHIBITORS AND METHODS OF USE

CROSS REFERENCE TO RELATED APPLICATIONS

This application is a national stage application under 35 U.S.C. 371 of PCT Application No. PCT/US2006/038727 having an international filing date of Oct. 3, 2006, which designated the United States, which PCT application claimed the benefit of U.S. Provisional Application No. 60/723,354 filed Oct. 3, 2005, the entire disclosure of each of which is hereby incorporated herein by reference.

REFERENCE TO SEQUENCE LISTING

This application contains a Sequence Listing submitted as an electronic text file named "4152-16-PCT.ST25.txt", having a size in bytes of 22KB, and created on Oct. 3, 2006. The information contained in this electronic file is hereby incorporated by reference in its entirety pursuant to 37 CFR §1.52(e)(5).

FIELD OF THE INVENTION

This invention generally relates to polymer sFlt-1 conjugates, variants of sFlt-1, compositions comprising such agents, and uses of such agents.

BACKGROUND OF THE INVENTION

Vascular endothelial growth factor (VEGF) is a major inducer of angiogenesis or new blood vessel formation. This protein and members of the VEGF family play critical roles during normal embryonic vasculature development and are also associated with a number of angiogenesis related pathological conditions including cancer, rheumatoid arthritis and diabetic retinopathy. VEGF exerts its biological activity by binding to two tyrosine kinase receptors, VEGF-R1 (Flt-1) and VEGF-R2 (Flk-1/KDR). Both receptors belong to the type III tyrosine kinase family and are characterized by an extracellular domain consisting of seven immunoglobulin (Ig)-like loops, a transmembrane domain and a split kinase domain within the cytoplasmic moiety (Shibuya, 2001). Several of the biochemical characteristics of the extracellular or soluble domain of Flt-1 (sFlt-1) make it a potential antagonist of VEGF activity and therefore a potential therapeutic agent. First, sFlt-1 has a much higher affinity for VEGF than Flk-1/KDR and does not need accessory proteins for ligand binding. Second, sFlt-1 also binds many of the VEGF isoforms along with other members of the VEGF family including VEGF-B and placenta growth factor (PIGF) (Hornig et al. 1999).

For a sFlt-1-based protein therapeutic to be practical for human use, it needs to have good in vivo stability and a long circulating half-life, particularly if given chronically. Unfortunately, most recombinant proteins have relatively short residence times in circulation, on the order of hours.

Therapeutic proteins are typically, but not exclusively, administered by injection. Introduction of proteins into circulation exposes them to numerous cell types, enzymes and routes of extravasation that contribute to their rapid clearance or catabolism. The protein may be attacked by plasma proteases or bind plasma proteins. Cell binding may result in the uptake of the protein via endocytotic or pinocytotic mechanisms, with the end result being degradation by lysosomal proteases. Proteins that avoid capture by these cells may pass out of the circulation via uptake by the liver, the lymphatic system or renal glomeruli (Sheffield, 2001).

Because of these rapid clearance mechanisms, circulating concentrations of injected proteins change constantly, often by several orders of magnitude, over a 24 hr period. These fluctuations can lead to decreased efficacy and increased frequency of adverse side effects for protein therapeutics. Most protein products currently on the market require frequent injections, usually multiple times per week. This dosing regimen is painful, inconvenient for the patient, and may not provide the optimum therapeutic benefit. In the case of a chronic indication such as cancer or RA, treatment could last for years.

Covalent modification of proteins with PEG has proven to be a useful method to extend the circulating half-lives of proteins in the body (Abuchowski et al., 1984; Meyers et al., 1991; Keating et al., 1993). Several PEGylated proteins are approved for use in humans or are in human clinical trials (Harris et al., 2003). Covalent attachment of PEG to a protein increases the protein's effective size and reduces its rate of clearance from the body, presumably through interference with protein removal pathways, including kidney glomerular filtration, proteolytic degradation as well as active clearance via specific receptors.

PEGs are commercially available in several sizes and shapes, allowing the circulating half-lives of PEG-modified proteins to be tailored for individual indications through the use of different PEGs. PEGylation increases a protein's effective molecular weight more than would be expected based on the molecular weight of the PEG moiety due to the water of hydration associated with the PEG group. For example, attachment of a single 5 kDa PEG to a 36 kDa protein increases the effective molecular weight of the complex to greater than 100 kDa, as measured by size-exclusion chromatography (Fee, 2003). When administered by subcutaneous injection, PEGylated proteins are slowly absorbed from the injection site, thus avoiding the serum "spikes" seen after subcutaneous injection of an unmodified protein. This "controlled release" of the PEGylated protein results in a more constant serum level, thus prolonging or increasing the drug's pharmacologic activity while minimizing the side effects typically seen with fluctuations in the drug concentrations. Other documented in vivo benefits of PEG modification include an increase in protein solubility, enhanced stability (possibly due to protection from proteases) and a decrease in immunogenicity (Keating et al., 1993).

SUMMARY OF THE INVENTION

One embodiment of the present invention relates to a PEGylated sFlt-1 protein, homologue thereof, or truncated form thereof, wherein the protein binds to VEGF. In one aspect of this embodiment, the truncated form of sFlt-1 comprises at least domains 2 and 3 of sFlt-1. In another aspect, the truncated form of sFlt-2 further comprises any one or more of domains 1, 4, 5 or 6. In another aspect, the truncated form of sFlt-1 is selected from the group consisting of: domains 1-3, domains 1-4, domains 1-5, domains 1-6, domains 2-3, domains 2-4, domains 2-5, and domains 2-6. In yet another aspect, the truncated form of sFlt-1 further comprises at least a portion of an additional sFlt-1 domain. The portion of the additional domain can include, but is not limited to, the first three or last three amino acids of the additional domain.

In one aspect of this embodiment, at least one PEG is attached to the sFlt-1 protein or truncated form thereof at a site selected from: the N-terminal amino acid, a native cysteine residue, a non-native cysteine residue, a lysine, and an unnatural amino acid substituted or inserted into said sFlt-1 or truncated form thereof. In another aspect, the sFlt-1 protein or homologue or truncated form thereof is PEGylated by a method selected from: amine reactive PEGylation, cysteine reactive PEGylation, carboxyl-reactive PEGylation, PEGylation of an unnatural amino acid substituted or inserted into said sFlt-1 or truncated form thereof, arginines reactive PEGylation, hydroxyl reactive PEGylation, oxidized carbohydrate reactive PEGylation, N-terminal serine PEGylation, enzyme catalyzed PEGylation and multi-functional PEGylation.

In one aspect of this embodiment, the sFlt-1 comprises an amino acid sequence of SEQ ID NO:2.

Another embodiment of the present invention relates to a composition comprising any one or more of the above-described PEGylated sFlt-1 proteins, homologues thereof, or truncated forms thereof, and a pharmaceutically acceptable carrier.

Yet another embodiment of the present invention relates to a cysteine variant of sFlt-1 (SEQ ID NO:2) or a homologue or truncated form thereof, wherein a cysteine residue is substituted for at least one amino acid located in at least one region of sFlt-1 selected from: the surface of sFlt-1, a region that is not required for structural integrity of sFlt-1, and a region that is not required for VEGF binding by sFlt-1; wherein said variant has biological activity in vitro as measured by the binding of the variant to VEGF.

In one aspect of this embodiment, the truncated form of sFlt-1 comprises at least domains 2 and 3 of sFlt-1. In another aspect, the truncated form of sFlt-1 further comprises any one or more of domains 1, 4, 5 or 6. In another aspect, the truncated form of sFlt-1 is selected from the group consisting of: domains 1-3, domains 1-4, domains 1-5, domains 1-6, domains 2-3, domains 2-4, domains 2-5, and domains 2-6. In yet another aspect, the truncated form of sFlt-1 further comprises at least a portion of an additional sFlt-1 domain. The portion of the additional domain can include, but is not limited to, the first three or last three amino acids of the additional domain.

In one aspect of this embodiment, a cysteine residue is substituted for at least one amino acid that is a glycosylation site in sFlt-1. In another aspect, a cysteine residue is substituted for at least one amino acid in a region between any one or more of: domains 1 and 2, domains 2 and 3, domains 3 and 4, domains 4 and 5, and domains 5 and 6. In yet another aspect, a cysteine residue is substituted for at least one amino acid selected from: N100, N164, N196, N251, N323, N402, N417, N474, N547, N597, N620 and N625. In another aspect, a cysteine residue is inserted or substituted for at least one amino acid located in the N-terminal region of sFlt-1 or a truncated form thereof or the C-terminal region of sFlt-1 or a truncated form thereof. In yet another aspect, a cysteine residue is inserted at the N-terminus of sFlt-1 or a truncated form thereof or at the C-terminus of Flt-1 or a truncated form thereof. In another aspect, a cysteine residue is substituted for an amino acid selected from: G26, D31, N100, N164, N196, N323, and H338.

In one aspect of this embodiment, the substituted or inserted cysteine residue is modified with a cysteine-reactive moiety. In another aspect, the substituted or inserted cysteine residue is modified with polyethylene glycol.

Another embodiment of the present invention relates to a composition comprising any one or more of the above-described variants and a pharmaceutically acceptable carrier.

Yet another embodiment of the present invention relates to a method to inhibit VEGF activity. The method includes contacting VEGF with any of the above-described PEGylated sFlt-1 proteins, homologues thereof, truncated forms thereof, any of the above-described cysteine variants, and/or any of the above-described compositions. In one aspect of this embodiment, the patient that has a disease or condition where inhibition of VEGF will reduce or prevent at least one symptom of the disease or condition.

Another embodiment of the present invention relates to a method to inhibit angiogenesis in a patient. The method includes administering to a patient any of the above-described PEGylated sFlt-1 proteins, homologues thereof, truncated forms thereof, any of the above-described cysteine variants, and/or any of the above-described compositions.

Another embodiment of the present invention relates to a method to treat rheumatoid arthritis. The method includes administering to a patient that has or is at risk of developing rheumatoid arthritis, any of the above-described PEGylated sFlt-1 proteins, homologues thereof, truncated forms thereof, any of the above-described cysteine variants, and/or any of the above-described compositions.

Yet another embodiment of the present invention relates to a method to treat a cancer. The method includes administering to a patient that has or is at risk of developing a cancer, any of the above-described PEGylated sFlt-1 proteins, homologues thereof, truncated forms thereof, any of the above-described cysteine variants, and/or any of the above-described compositions.

Another embodiment of the present invention relates to the use of any of the above-described PEGylated sFlt-1 proteins, homologues thereof, truncated forms thereof, any of the above-described cysteine variants, and/or any of the above-described compositions, in a medicament for inhibiting VEGF activity.

DETAILED DESCRIPTION OF THE INVENTION

This invention describes novel polymer sFlt-1 conjugates that have been created by the chemical coupling of one or more polymers such as polyethylene glycol moieties to sFlt-1, as well as novel variants of sFlt-1 developed by the present inventors. The present invention also described methods of making and using such sFlt-1 conjugates and variants. Based on the present inventors work, these novel sFlt-1-based protein polymer conjugates will have improved stability, higher potency, greater solubility, longer circulating half-lives for less frequent dosing, and reduced antigenicity as compared to the parent molecule. Various aspects of the present invention are described in detail below, although particular examples are not intended to limit the scope of the present invention.

General Definitions

As used herein, reference to an isolated protein or polypeptide in the present invention, including a sFlt-1 protein described particularly herein, includes full-length proteins, fusion proteins, or any fragment (truncated form) or homologue of such a protein. Such a protein can include, but is not limited to, purified proteins, recombinantly produced proteins, membrane bound proteins, proteins complexed with lipids, soluble proteins and isolated proteins associated with other proteins. More specifically, an isolated protein according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. In addition, and again by way of example, a "human sFlt-1 protein" or a protein "derived from" a human sFlt-1 protein refers to a sFlt-1 protein (generally including a homologue of a naturally occurring sFlt-1 protein) from a human (*Homo sapiens*) or to a sFlt-1 protein that has been otherwise produced from the knowledge of the structure (e.g., sequence) and perhaps the function of a naturally occurring sFlt-1 protein from *Homo sapiens*. In other words, a human sFlt-1 protein includes any sFlt-1 protein that has substantially similar structure and function of a naturally occurring sFlt 1 protein from *Homo sapiens* or that is a biologically active (i.e., has biological activity) homologue of a naturally occurring sFlt-1 protein from *Homo sapiens* as described in detail herein. As such, a human sFlt-1 protein can include purified, partially purified, recombinant, mutated/modified and synthetic proteins. According to the present invention, the terms "modification" and "mutation" can be used interchangeably, particularly with regard to the modifications/mutations to the amino acid sequence of protein (or nucleic acid sequences) described herein. An isolated protein useful as an antagonist or agonist according to the present invention can be isolated from its natural source, produced recombinantly or produced synthetically.

As used herein, the term "homologue" is used to refer to a protein or peptide which differs from a naturally occurring protein or peptide (i.e., the "prototype" or "wild-type" protein) by modifications, including minor modifications, to the naturally occurring protein or peptide, but which maintains the basic protein and side chain structure of the naturally occurring form. Such changes include, but are not limited to: changes in one or a few (i.e., 1, 2, 3, 4, 5, 6, 7, 8, 9 or 10) amino acid side chains; changes one or a few amino acids, including deletions (e.g., a truncated form of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have either enhanced, decreased, or substantially similar properties as compared to the naturally occurring protein or peptide. A homologue can include an agonist of a protein or an antagonist of a protein.

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

In one embodiment, a homologue of a given protein comprises, consists essentially of, or consists of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homologue comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

According to the present invention, an isolated sFlt-1 protein, including a biologically active homologue or fragment thereof, has at least one characteristic of biological activity of activity the wild-type, or naturally occurring sFlt-1 protein (which can vary depending on whether the homologue or fragment is an agonist or antagonist of the protein, or whether an agonist or antagonist mimetic of the protein is described). In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Modifications, activities or interactions which result in a decrease in protein expression or a decrease in the activity of the protein, can be referred to as inactivation (complete or partial), down-regulation, reduced action, or decreased action or activity of a protein. Similarly, modifications, activities or interactions which result in an increase in protein expression or an increase in the activity of the protein, can be referred to as amplification, overproduction, activation, enhancement, up-regulation or increased action of a protein. The biological activity of a sFlt-1 protein according to the invention can be measured or evaluated using any assay for the biological activity of the protein as known in the art. Such assays are known in the art. A preferred sFlt-1 in vitro bioassay is the inhibition of VEGF-stimulated proliferation of human umbilical vein endothelial cells, although other assays will be known to those of skill in the art.

As used herein, reference to an "agonist" of a sFlt-1 protein refers to any compound that is characterized by the ability to agonize (e.g., stimulate, induce, increase, enhance, or mimic) the biological activity of the naturally occurring protein, and includes any homologue, binding protein (e.g., an antibody), agent that interacts with a protein or receptor bound by the protein, or any suitable product of drug/compound/peptide design or selection which is characterized by its ability to agonize (e.g., stimulate, induce, increase, enhance) the biological activity of the naturally occurring sFlt-1 protein in a manner similar to the natural agonist, which is the reference protein.

Similarly, reference to an "antagonist" refers to any compound which inhibits (e.g., antagonizes, reduces, decreases, blocks, reverses, or alters) the effect of a given agonist of a sFlt-1 protein (including the protein itself) as described above. More particularly, an antagonist is capable of acting in a manner relative to the activity of the sFlt-1 protein, such that the biological activity of a natural agonist or sFlt-1 protein, is decreased in a manner that is antagonistic (e.g., against, a reversal of, contrary to) to the natural action of the protein. Such antagonists can include, but are not limited to, a protein, peptide, or nucleic acid (including ribozymes, RNAi, aptamers, and antisense), antibodies and antigen binding fragments thereof, or product of drug/compound/peptide design or selection that provides the antagonistic effect.

Homologues of a given protein, including peptide and non-peptide agonists and antagonists (analogs), can also be products of drug design or selection and can be produced using various methods known in the art. Such homologues can be referred to as mimetics. Various methods of drug design, useful to design or select mimetics or other therapeutic compounds useful in the present invention are disclosed in Maulik et al., 1997, *Molecular Biotechnology: Therapeutic Applications and Strategies*, Wiley-Liss, Inc., which is incorporated herein by reference in its entirety.

As used herein, a mimetic refers to any peptide or non-peptide compound that is able to mimic the biological action of a naturally occurring peptide, often because the mimetic has a basic structure that mimics the basic structure of the naturally occurring peptide and/or has the salient biological properties of the naturally occurring peptide. Mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example. Such mimetics can be designed, selected and/or otherwise identified using a variety of methods known in the art.

A mimetic can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In accordance with the present invention, an isolated polynucleotide (also referred to as an isolated nucleic acid molecule) is a nucleic acid molecule that has been removed from its natural milieu (e.g., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. A polynucleotide useful in the present invention can include a portion of a nucleic acid sequence (sense or non-sense strand) that is suitable for use as a hybridization probe or PCR primer for the identification of a full-length gene (or portion thereof), or to encode a protein or fragment (truncated form) or homologue thereof. An isolated nucleic acid molecule that includes a gene is not a fragment of a chromosome that includes such gene, but rather includes the coding region and regulatory regions associated with the gene, but no additional genes naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. Preferably, an isolated nucleic acid molecule of the present invention is produced using recombinant DNA technology (e.g., polymerase chain reaction (PCR) amplification, cloning) or chemical synthesis.

The minimum size of a nucleic acid molecule or polynucleotide of the present invention is a size sufficient to encode a protein having a desired biological activity, or sufficient to form a probe or oligonucleotide primer that is capable of forming a stable hybrid with the complementary sequence of a nucleic acid molecule encoding the natural protein (e.g., under moderate, high or very high stringency conditions). If the polynucleotide is an oligonucleotide probe or primer, the size of the polynucleotide can be dependent on nucleic acid composition and percent homology or identity between the nucleic acid molecule and a complementary sequence as well as upon hybridization conditions per se (e.g., temperature, salt concentration, and formamide concentration). The minimum size of a polynucleotide that is used as an oligonucleotide probe or primer is at least about 5 nucleotides in length, and preferably ranges from about 5 to about 50 or about 500 nucleotides or greater, including any length in between, in whole number increments (i.e., 5, 6, 7, 8, 9, 10, . . . 33, 34, . . . 256, 257, . . . 500). There is no limit, other than a practical limit, on the maximal size of a nucleic acid molecule of the present invention, in that the nucleic acid molecule can include a portion of a protein-encoding sequence or a nucleic acid sequence encoding a full-length protein.

As used herein, stringent hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M $Na^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M $Na^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

In one embodiment of the present invention, any of the sFlt-1 amino acid sequences described herein, including truncated forms and homologues of such sequences, can be produced with from at least one, and up to about 20, additional heterologous amino acids flanking each of the C- and/or N-terminal end of the given amino acid sequence. The resulting protein or polypeptide can be referred to as "consisting essentially of" a given amino acid sequence. According to the present invention, the heterologous amino acids are a sequence of amino acids that are not naturally found (i.e., not found in nature, in vivo) flanking the given amino acid sequence or which would not be encoded by the nucleotides that flank the naturally occurring nucleic acid sequence encoding the given amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a given amino acid sequence that can be flanked by from at least one, and up to as many as about 60, additional heterologous nucleotides at each of the 5' and/or the 3' end of the nucleic acid sequence encoding the given amino acid sequence. The heterologous nucleotides are not naturally found (i.e., not found in nature, in vivo) flanking the nucleic acid sequence encoding the given amino acid sequence as it occurs in the natural gene.

Structural Information Regarding sFlt-1

Naturally occurring sFlt-1 was first isolated from HUVEC conditioned medium in 1996 but its existence was predicted in 1990 based on cDNA clones (Kendall et al., 1996; Shibuay et al., 1990). sFlt-1 appears to be the result of an alternatively splice variant of sFlt-1 rather than the product of proteolytic activity on the cell surface. This variant has a unique C-terminal intron-derived extension of 31 amino acids (Kendall et al., 1993). While the actual physiological role of sFlt-1 remains unclear, recent experiments suggest that sFlt-1 may be acting as a decoy receptor to reduce VEGF availability to avoid overgrowth of the endothelial cells (Hiratsuka et al., 1998). The primary amino acid sequence of human sFlt-1 is shown in SEQ ID NO:2. SEQ ID NO:2 is encoded by a nucleic acid molecule represented herein by SEQ ID NO:1. The predicted amino acid regions that male up the Ig-like domains are as follows: Domain 1: Residues 32-123 of SEQ ID NO:2; Domain 2: Residues 151-214 of SEQ ID NO:2; Domain 3: Residues 230-327 of SEQ ID NO:2; Domain 4: Residues 335-421 of SEQ ID NO:2; Domain 5: Residues 428-553 of SEQ ID NO:2, and Domain 6: Residues 556-654 of SEQ ID NO:2. This numbering system assumes that Residue 1 of SEQ ID NO:2 is the start of the signal sequence that includes residues 1-26. Potential disulfides include C53-107, C158-C207, C252-C311, C454-535 and C577-C636, all positions being given with respect to SEQ ID NO:2. Potential glycosylation sites include N100, N164, N196, N251, N323, N402, N417, N474, N547, N597, N620 and N625 (See ExPASy Swiss-Prot: entry P17948), all with respect to SEQ ID NO:2.

A variety of sFlt-1 constructs have been made, in order to identify the extracellular Ig-like loops that are directly involved in the interaction with ligands. These experiments showed that the second Ig-like extracellular domain determines the ligand binding and specificity of sFlt-1 (Davis-Smith et al., 1996). The third Ig-like domain is necessary for high affinity binding and the fourth is needed for receptor dimerization (Barleon et al., 1997; Tanaka et al., 1997). Crystallography studies with a sFlt-1 receptor:VEGF complex showed analogous results (Wiesmann et al., 1997). Truncated version of sFlt-1, consisting only of domains 2 and 3, had an affinity for VEGF that was essentially equal to the full-length molecule (Barleon et al., 1997).

The present invention encompasses a variety of sFlt-1 protein truncates (truncated forms) that are useful for PEGylation according to the present invention. Variations include sFlt-1 protein truncates consisting essentially of or consisting of domains 1-3, 1-4, 1-5, 1-6, 2-3, 2-4, 2-5, and 2-6, or fusions of the domains such as 2-3+5 and the like, where the protein retains VEGF binding activity. In one embodiment, a truncated form includes at least domains 2 and 3 of sFlt-1. In another embodiment, a truncated form includes one or more of domains 1, 4, 5 or 6 of sFlt-1. Alternatively, a portion of a domain may be included in the construct (for example, domains 1-3 and the first 3 amino acids of domain 4). In one embodiment, the portion of the additional domain includes the first one, two or three, or the last one, two or three amino acids of the additional domain.

The present invention also includes homologues of any of these sFlt-1 proteins and truncated forms thereof. Homologues are described in detail above. Preferably, homologues of sFlt-1 proteins have sFlt-1 biological activity. For example, sFlt-1 analog that has in vitro bioactivity ($IC_{50}$) of less than about 1000 ng/mL in a sFlt-1-dependent in vitro bioassay. As discussed above, a preferred sFlt-1 in vitro bioassay is the inhibition of VEGF-stimulated proliferation of human umbilical vein endothelial cells, although other assays will be known to those of skill in the art.

Polyethylene Glycol (PEG) Conjugation

A preferred embodiment of the present invention is a PEGylated sFlt-1 protein. A more preferred embodiment is a monoPEGylated sFlt-1 protein. MonoPEGylated indicates that the protein is modified with a single PEG (e.g., at a single site in the protein). It is well known in the art that PEGylated proteins can have widely varying in vitro bioactivities due to where PEG attaches to the protein. A preferred composition of the present invention is a PEGylated or monoPEGylated sFlt-1 protein that has in vitro bioactivity ($IC_{50}$) of less than about 1000 ng/mL in a sFlt-1-dependent in vitro bioassay (suitable in vitro bioassays are discussed above). A more preferred composition is a PEGylated or monoPEGylated sFlt-1 protein with an $IC_{50}$ of less than about 300 ng/mL in an in vitro bioassay. An even more preferred composition is a PEGylated or monoPEGylated sFlt-1 protein with an $IC_{50}$ less than about 100 ng/mL in an in vitro bioassay. The Examples presented below teach preferred methods for preparing PEGylated and monoPEGylated sFlt-1 proteins (including truncated forms and other homologues thereof) that have the in vitro bioactivities described above.

A PEG moiety can be attached to the N-terminal amino acid, a cysteine residue (either native or non-native), lysines or other reactive native or non-native amino acids in the protein's primary sequence. More specifically, preferred PEGylation sites include any surface exposed amino acid that is not required for biological activity or structural integrity. Preferred sites also include the N-terminal and C-terminal regions of the sFlt-1 protein or truncate thereof (including the N- and/or C-terminal amino acids of the sFlt-1 protein or truncate), the amino acids that connect any of the domains, a native cysteine residue, a non-native cysteine residue (cysteine variants described in more detail below), a lysine, a the glycosylation site that is present on sFlt-1 and sFlt-1 variants, and a non-native amino acid substituted or inserted into the sFlt-1 protein or truncated form thereof.

A non-native amino acid is defined as an amino acid that is not normally located at that position in the protein, an amino acid analog that is not commonly seen in native proteins, or an amino acid or amino acid analog that has been chemically modified to allow conjugation with a polymer such as polyethylene glycol.

Amine Reactive PEG Reagents for Modification of sFlt-1

The most common route for PEG conjugation of proteins is to use a PEG with a functional group that react with lysines and/or the N-terminal amino acid group. The literature describes more than a dozen such procedures (see reviews by Hooftman et al., 1996; Delgato et al., 1992; and Zalipsky, 1995). Examples of amine-reactive PEGs include PEG dichlorotriazine, PEG tresylate, PEG succinimidyl carbonate, PEG benzotriazole carbonate, PEG p-nitrophenyl carbonate, PEG carbonylimidazole, PEG succinimidyl succinate, PEG propionaldehyde, PEG acetaldehyde, and PEG hydroxysuccinimide.

sFlt-1 has 44 potential sites (the N-terminus and 43 lysines) for conjugation with an amine reactive PEG. Any one or more of these sites are expressly encompassed by the present invention for modification. Multiple attachments may occur if the protein is exposed to an excess amount of PEGylation reagent. Preferably, the sFlt-1 PEG conjugate would have 1-5 PEGs attached to the protein (i.e., 1, 2, 3, 4 or 5 PEGs), more preferred would be 1-3 attachments, and most preferred 1-2 attachments. Conditions can be adjusted to limit the number of attachments or the site of attachments. The number of attachments can be titrated by varying the molar ratios of the PEG:Protein. Preferred ratios can be determined experimentally. A second method for varying the number of attachments is by modifying the reaction conditions. For example, the coupling can be preferentially directed to the alpha-terminus of a protein chain by performing the reaction at a pH lower than 7 and preferably below 6.5. Above pH 8, the epsilon-NH3 groups found on the lysines will be most reactive. (Morpurgo and Veronese, 2004). A third approach to controlling the number or location of the PEG conjugates is to conduct the PEGylation in the presence of a substrate, reversible inhibitor or binding protein so that the active site is protected during coupling. A fourth approach to controlling the number of attachments involves using a larger PEG. For example when interferon-alpha is modified with a small linear polymer, up to 11 positional isomers are present in the final mixture. When interferon-alpha is modified with a larger 40 kDa branched PEG, only four main positional isomers are present in the mono-PEGylated protein (Monkarsh et al., 1997, Foser et al. 2003, Baillon et al. 2003). A fifth method to control the number of attached PEGs is to use column chromatography procedures (ion exchange, size exclusion or hydrophobic interaction) to purify a sFlt-1 conjugate containing the desired number of PEG molecules from a more complex sFlt-1-PEG mixture.

PEG-Protein Conjugates Using Cysteine-Reactive PEGs

Another method for PEGylating proteins covalently attaches PEG to cysteine residues using thiol-reactive PEGs. A number of highly specific, thiol-reactive PEGs with different reactive groups (e.g., PEG-ortho-pyridyl-disulfide, PEG-maleimide, PEG-vinylsulfone and PEG-iodoacetamide), different size PEGs (2-40 kDa), different shaped PEGs (linear or branched) and different end group (hydroxyl, carboxylic acid, methoxy or other alkoxy group) are commercially available. The conjugates are hydrolytically stable and the PEGylation reactions can be performed at neutral pH.

Cysteine residues in most proteins participate in disulfide bonds and are not available for derivatization. Through in vitro site-directed mutagenesis techniques, additional cysteine residues can be introduced (i.e., by insertion between, before or after a native residue, or by substitution of a cysteine for a non-cysteine native residue) at any specified site on the protein, wherein the added cysteine does not substantially negatively affect the biological activity of the protein. Preferred sites for introduction of a non-native cysteine to sFlt-1 are discussed below. The newly added "free" cysteine will serve as the site for the specific attachment of a PEG molecule, thus avoiding the product heterogeneity that is often seen with amine PEGylation reactions. The added cysteine must be exposed on the protein's surface and be accessible for PEGylation for this method to be successful. If the chosen site is non-essential with respect to folding or bioactivity of the protein, then the PEGylated protein will display wild type (normal) or near wild type in vitro bioactivity.

A free thiol group can also be introduced into the primary amino acid sequence of a protein by chemical modification of lysine. One such example involves treatment of the protein with Traut's reagent. Alternatively, the protein can be treated with reagents such as N-succinimidyl S-acetylthioacetate (SATA) or N-succinimidyl S-acetylthiopropionate (SATP) that introduce a protected sulfhydryl which can be deprotected prior to exposure to a thiol reactive PEG. Alternatively, a "free" cysteine can be introduced by deleting or mutating a native cysteine (that normally forms a disulfide bond) to another amino acid such as a serine or alanine so that an odd number of cysteines are present in the protein's primary sequence.

It is also possible to genetically introduce two or more additional cysteines that are not able to disulfide bond with each other. In this case, two PEGs (or even numbers of PEGs) can be specifically attached to the protein. Alternatively, a native, non-essential disulfide bond can be reduced, resulting in two free cysteine residues that are available for thiol specific PEGylation.

Free thiol groups can also be introduced by chemical conjugation of a peptide to a protein where the peptide contains a free cysteine group or a cysteine group modified with a reversible thiol blocking agent.

Preferred Sites for Thiol-Specific PEGylation

In general, a cysteine substitution or insertion can be made for or between, respectively, any amino acid that is: 1) located on the surface of sFlt-1, 2) not required for the structural integrity of sFlt-1 and 3) not required for VEGF binding. Non-essential amino acids can be identified by performing cysteine-scanning mutagenesis on the target protein and measuring effects on biological activity. Cysteine-scanning mutagenesis entails adding or substituting cysteine residues for individual amino acids in the polypeptide chain and determining the effect of the cysteine substitution on biological activity. Cysteine scanning mutagenesis is similar to alanine-scanning mutagenesis (Cunningham et al., 1991), except that target amino acids are individually replaced with cysteine rather than alanine residues. The terms "cysteine variant" and "cysteine mutein" can be used interchangeably herein, and refer to homologues of a natural protein (sFlt-1) that have an amino acid sequence that differs from the amino acid sequence of the natural protein by the presence of at least one additional cysteine residue, which can be substituted or inserted, or by the creation of a "free" native cysteine by deletion of another cysteine in the protein.

Glycosylation sites are attractive sites for attaching PEG molecules because these sites are surface exposed and the natural protein can tolerate bulky sugar groups at these positions. sFlt-1 has 12 potential N-linked glycosylation sites, each of which is expressly encompassed for modification by cysteine substitution or insertion and PEGylation according to the present invention. These 12 potential sites are: N100, N164, N196, N251, N323, N402, N417, N474, N547, N597, N620 and N625, with respect to SEQ ID NO:2. The N- and C-termini regions of sFlt-1 (e.g., any one or more of the first ten (position 1, 2, 3, 4, 5, 6, 7, 8, 9 or 10 with respect to SEQ ID NO:2) or last ten (position 678, 679, 680, 681, 682, 683, 684, 685, 686, or 687 with respect to SEQ ID NO:2) amino acids of sFlt-1) are also preferred sites for site-directed PEGylation, which includes adding a cysteine preceding the first amino acid or following the last amino acid of sFlt-1 (SEQ ID NO:2) or of the truncated form thereof. Cysteine insertions within the primary amino acid sequence of a protein are also reasonable sites for thiol specific PEGylation if the biological activity or protein's conformation is not negatively affected by the cysteine insertions. Particularly preferred sites for cysteine modification by insertion or substitution include an amino acid in the sequence between domains 1 and 2 (any one or more of amino acid residues 124 to 150), between domains 2 and 3 (any one or more of amino acid residues 215 to 229), between domains 3 and 4 (any one or more of amino acid residues 328 to 334), between domains 4 and 5 (any one or more of amino acid residues 422 to 427), or between domains 5 and 6 (any one or more of amino acid residues 554 to 555).

Preferred sites for cysteine modification of sFlt-1 according to the present invention, which include residues in which a cysteine residue can be substituted for a non-cysteine residue, or residues between which a cysteine residue can be inserted, include (with respect to SEQ ID NO:2): S27, K28, L29, K30, D31, P32, E33, L34, S35, L36, K37, G38, T39, Q40, H41, I42, M43, Q44, A45, G46, Q47, T48, L49, H50, L51, Q52, R54, G55, E56, A57, A58, H59, K60, W61, S62, L63, P64, E65, M66, V67, S68, K69, E70, S71, E72, R73, L74, S75, I76, T77, K78, S79, A80, G82, R83, N84, G85, K86, Q87, F88, S90, T91, L92, T93, L94, N95, T96, A97, Q98, A99, N100, H101, T102, G103, F104, Y105, S106, K108, Y109, L110, A111, V112, P113, T114, S115, K116, K117, K118, E119, T120, E121, S122, A123, I124, Y125, I126, F127, I128, S129, D130, T131, G132, R133, P134, F135, V136, E137, M138, Y139, S140, E141, I142, P143, E144, I145, I146, H147, M148, T149, E150, G151, R152, E153, L154, V155, I156, P157, R159, V160, T161, S162, P163, N164, I165, T166, V167, T168, L169, K170, K171, F172, P173, L174, D175, T176, L177, I178, P179, D180, G181, K182, R183, I184, I185, W186, D187, S188, R189, K190, G191, F192, I193, I194, S195, N196, A197, T198, Y199, K200, E201, I202, G203, L204, L205, T206, E208, A209, T210, V211, N212, G213, H214, L215, Y216, K217, T218, N219, Y220, L221, T222, H223, R224, Q225, T226, N227, T228, I229, I230, D231, V232, Q233, I234, S235, T236, P237, R238, P239, V240, K241, L242, L243, R244, G245, H246, T247, L248, V249, L250, N251, T253, A254, T255, T256, P257, L258, N259, T260, R261, V262, Q263, M264, T265, W266, S267, Y268, P269, D270, E271, K272, N273, K274, R275, A276, S277, V278, R278, R280, R281, I282, D283, Q284, S285, N286, S287, H288, A289, N290, I291, F292, Y293, S294, V29, L296, T297, I298, D299, K300, M301, Q302, N303, K304, D305, K306, G307, L308, Y309, T310, R312, V313, R314, S315, G316, P317, S318, F319, K320, S322, V322, N323, T324, S325, V326, H327, I328, Y329, D330, K332, A332, F333, I334, T335, V336, K337, H338, R339, K340, Q341, Q342, V343, L344, E345, T346, V347, A348, G349, K350, R351, S352, Y353, R354, L355, S356, M357, K358, V359, and K360.

Other particularly preferred sites for cysteine modification include, but are not limited to, the following specific residues of sFlt-1 (with respect to SEQ ID NO:2): G26, D31, N100, N164, N196, N323, and H338.

These described preferred sites for full length sFlt-1 also apply to truncated forms of sFlt-1 which include variants that are missing one or more of the native six IgG-like domains but retain VEGF binding ability.

Carboxyl-Reactive PEGs for PEGylation

PEG-hydrazide can be used to PEGylate the carboxyl groups in presence of N,N'-dicyclohexylcarbodiimide (DCC), or in presence of a water soluble coupling agent such as N-(-3-dimethylaminopropyl)-N'-ethylcarbodiimide hydrochloride (EDC). The carboxyl groups of a protein when activated with EDC at an acidic pH (pH 4.5-5) react readily with PEG-hydrazide, whereas amino groups of the protein are protonated and unreactive. The extracellular domain of Flt-1 has 28 aspartic acids and 42 glutamic acids, each of which is expressly encompassed for modification according to this embodiment.

Unnatural Amino Acid PEGylation

Similar to the genetically engineered cysteine mutations for site-specific PEGylation, researchers have reported the specific incorporation of unnatural amino acids into proteins expressed in yeast (Deiters et al., 2004). Specifically para-azidophenylalanine was substituted into a protein at certain sites determined by the positioning of the amber codon. The reactive group on the amino acid analog was used in a mild [3+2] cycloaddition reaction with an alkyne derivatized PEG reagent to allow for site-specific conjugation.

Arginine-Reactive PEGs for PEGylation

A less preferred approach is the attachment of the PEG moiety on the arginine side chain using PEG-1-3-dioxo compounds such as PEG-phenylglioxate. The disadvantages of this approach include long reaction times and limited specificity since other amino acids such as histidine and lysine, may be modified as well. The extracellular domain of Flt-1 has 37 arginines, which are expressly encompassed by the present invention as sites for modification according to this embodiment.

Hydroxyl-Reactive PEGs for PEGylation

PEG-isocyanate can be used to attach a PEG to a hydroxy group via a stable urethane linkage. The disadvantage of this approach is lack of specificity since it is also capable of reacting with amines. Thus, this reagent is more commonly used in PEGylation reactions involving polysaccharides or non-peptide drugs.

Oxidized Carbohydrate-Reactive PEGs for PEGylation

Oxidation of the carbohydrate residues or N-terminal serine or threonine is an alternative method for a site-specific PEGylation. Carbohydrate side chains can be oxidized with enzymes or chemically with sodium periodate to generate reactive aldehyde groups. These sites can be reacted with either PEG-hydrazine or PEG-amine to produce a reversible Schiff's base. These linkages are then reduced with sodium cyanoborohydride to a more stable alkyl hydrazide or in the case of the Schiff's base, a secondary amine. Multiple attachment sites are generated by this method but the PEG is localized on the carbohydrate chain rather than on the protein.

A similar approach takes advantage of an N-terminal serine or threonine. These amino acid residues can be converted by periodate oxidation to a glyoxylyl derivative that will also react with PEG-hydrazide or PEG-amine. Native sFlt-1 has an N-terminal serine, which is expressly encompassed by the present invention as a site for modification according to this embodiment.

Enzymatically Catalyzed PEGylation Reagents

A novel approach for PEGylation of proteins uses transglutaminase to modify glutamine residues so that they become reactive with alkylamine derivatives of PEG. (Sato 2002). The extracellular domain of Flt-1 has 27 glutamines, which are expressly encompassed by the present invention as sites for modification according to this embodiment.

Multifunctional PEGs

While a majority of the PEGylated proteins currently on the market have one or more PEGs per protein, it is also possible to construct protein conjugates with two or more proteins attached to one PEG moiety. Difunctional and heterofunctional PEGs are commercially available and can be used to covalently link two or more sFlt-1 variants. Accordingly, the present invention includes two or more sFlt-1 proteins, including truncated forms and homologues thereof, that are covalently linked by PEGs.

Methods of Use of the sFlt-1 Conjugates and Variants of the Invention

The present invention encompasses the use of any of the sFlt-1 conjugates and/or variants described herein, including combinations of any of such conjugates or variants, in a diagnostic, research or therapeutic method. In particular, encompassed by the invention are any methods for which a native sFlt-1 could be or is used, and in particular, includes any methods in which a VEGF inhibitor would be useful, and specifically, a long-acting VEGF inhibitor. Any combination of the above-described conjugates and variants can be used in a method of the present invention. In addition, sFlt-1 proteins, homologues and truncated forms thereof of the present invention can include any combination of variations and/or conjugations described herein.

A sFlt-1 conjugate and/or variant described herein can be administered to a patient in a composition. The composition can include a pharmaceutically acceptable carrier, which includes pharmaceutically acceptable excipients and/or delivery vehicles, for delivering the conjugate or variant to a patient. As used herein, a pharmaceutically acceptable carrier refers to any substance suitable for delivering a therapeutic composition useful in a method of the present invention to a suitable in vivo or ex vivo site. Preferred pharmaceutically acceptable carriers are capable of maintaining conjugate or variant of the present invention in a form that, upon arrival of the conjugate or variant at a target site in the patient (a target site can include systemic sites, as in the blood circulation), the conjugate or variant is or can be active at the site. Suitable excipients of the present invention include excipients or formularies that transport or help transport, but do not specifically target a conjugate or variant to a particular site (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

A pharmaceutically acceptable carrier can also include a controlled release formulation that is capable of slowly releasing a composition of the present invention into an animal. As used herein, a controlled release formulation comprises a conjugate or variant of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. A delivery vehicle of the present invention can be modified to target to a particular site in a patient, thereby targeting and making use of a conjugate or variant at that site. Suitable modifications include manipulating the chemical formula of the lipid portion of the delivery vehicle and/or introducing into the vehicle a targeting agent capable of specifically targeting a delivery vehicle to a preferred site, for example, a preferred cell type.

Compositions of the present invention can additionally include any other agent or compound that may be useful in a method of the present invention. For example, additional therapeutic agents for the inhibition of VEGF activity or angiogenesis, or for the treatment of a disease or condition associated with such activities, can be included.

A conjugate, variant, or composition comprising such conjugate or variant of the present invention, is administered to a subject in a manner effective to deliver the conjugate or variant to the subject in order to achieve an effect. Suitable administration protocols include any in vivo or ex vivo administration protocol. According to the present invention, an effective administration protocol (i.e., administering a composition of the present invention in an effective manner) comprises suitable dose parameters and modes of administration that result in delivery of an active conjugate or variant of the present invention to a subject, preferably so that the subject obtains some measurable, observable or perceived benefit from such administration. Effective dose parameters can be determined by experimentation using in vitro cell cultures, in vivo animal models, and eventually, clinical trials if the subject is human. Effective dose parameters used for native sFlt-1 or other VEGF proteins or similar compounds can also be used, although the conjugates and variants of the present invention should be longer-lasting and therefore, can be administered in smaller doses and/or less frequent intervals. Effective dose parameters can be determined using methods standard in the art for a particular disease or condition that the patient has or is at risk of developing. Such methods include, for example, determination of survival rates, side effects (i.e., toxicity) and progression or regression of disease.

Various suitable methods of in vivo administration of a composition include, but are not limited to, intravenous administration, intraperitoneal administration, intramuscular administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracerebral, nasal, oral, pulmonary administration, impregnation of a catheter, and direct injection into a tissue. All such types of administration are known in the art. A suitable single dose of a conjugate, variant, or composition of the invention typically comprises between about 0.01 microgram×kilogram$^{-1}$ and about 10 milligram×kilogram$^{-1}$ body weight of an animal.

Compositions of the present invention can be administered to any subject (individual, patient) that is a member of the Vertebrate class, Mammalia, including, without limitation, primates, livestock and domestic pets (e.g., a companion animal). Most typically, a patient will be a human patient. According to the present invention, administration of a composition is useful to inhibit angiogenesis, or more particularly, VEGF, in a subject (or tissue thereof). Typically, it is desirable to inhibit angiogenesis and/or to obtain a therapeutic benefit in the patient, and in the case of cancer, to reduce tumor burden in the patient (tumor numbers and/or volume), or to prevent further growth of the tumor in the patient (tumor stasis), or to obtain any therapeutic benefit in the patient (e.g., increased survival). In one embodiment, patients whom are suitable candidates for the method of the present invention include, but are not limited to, patients that have, or are at risk of developing (e.g., are predisposed to), any condition in which regulation of angiogenesis might be beneficial.

Conditions that are characterized or caused by abnormal or excessive angiogenesis, include, but are not limited to: cancer (e.g., activation of oncogenes, loss of tumor suppressors); infectious diseases (e.g., pathogens express angiogenic genes, enhance angiogenic programs); autoimmune disorders (e.g., activation of mast cells and other leukocytes), including rheumatoid arthritis; vascular malformations (e.g., Tie-2 mutation); DiGeorge syndrome (e.g., low VEGF and neuropilin-1 expression); HHT (e.g., mutations of endoglin or LK-1), cavernous hemangioma (e.g., loss of Cx37 and Cx40); atherosclerosis; transplant ateriopathy; obesity (e.g., angiogenesis induced by fatty diet, weight loss by angiogenesis inhibitors); psoriasis; warts; allergic dermatitis; scar keloids; pyogenic granulomas; blistering disease; Kaposi sarcoma in AIDS patients; persistent hyperplastic vitreous syndrome (e.g., loss of Ang-2 or VEGF164); diabetic retinopathy; retinopathy of prematurity; choroidal neovascularization (e.g., TIMP-3 mutation); primary pulmonary hypertension (e.g., germline BMPR-2 mutation, somatic EC mutation); asthma; nasal polyps; inflammatory bowel disease; periodontal disease; ascites; peritoneal adhesions; endometriosis; uterine bleeding; ovarian cysts; ovarian hyperstimulation; arthritis; synovitis; osteomyelitis; and/or osteophyte formation.

As such, a therapeutic benefit is not necessarily a cure for a particular disease or condition, but rather, preferably encompasses a result which most typically includes alleviation of the disease or condition or increased survival, elimination of the disease or condition, reduction of a symptom associated with the disease or condition (e.g., reduced angiogenesis), prevention or alleviation of a secondary disease or condition resulting from the occurrence of a primary disease or condition, and/or prevention of the disease or condition. As used herein, the phrase "protected from a disease" refers to reducing the symptoms of the disease; reducing the occurrence of the disease, and/or reducing the severity of the disease. Protecting a patient can refer to the ability of a composition of the present invention, when administered to a patient, to prevent a disease from occurring and/or to cure or to alleviate disease symptoms, signs or causes. As such, to protect a patient from a disease includes both preventing disease occurrence (prophylactic treatment) and treating a patient that has a disease (therapeutic treatment). A beneficial effect can easily be assessed by one of ordinary skill in the art and/or by a trained clinician who is treating the patient. The term, "disease" refers to any deviation from the normal health of a mammal and includes a state when disease symptoms are present, as well as conditions in which a deviation has occurred, but symptoms are not yet manifested.

Non-Limiting Example of a Long-Acting VEGF Inhibitor Useful in the Treatment of Rheumatoid Arthritis Rheumatoid arthritis (RA) is a chronic and destructive disease, which may affect any synovial joint in the body. A characteristic feature of RA is the change in the synovium as it becomes locally invasive at the interface with cartilage and bone. This destructive front (termed "pannus") causes the progressive erosion of the cartilage and bone, eventually leading to the physical deformities and disabilities typically seen with those patients suffering from long term arthritis. One of the earliest observed signs of RA is the development of a new vascular network within the synovium which serves to promote the delivery of cells and nutrients to the invading pannus (Rooney et al., 1988). The potential central role of neovascularization in RA has been demonstrated in a number of animal models of arthritis in which angiogenesis inhibitors were found to prevent the onset of collagen-induced arthritis and significantly suppress established disease (Oliver et al., 1994, De Bant et al., 2003; Arsenault et al., 1998; Sumariwalla et al., 2002, Matsuno et al., 2002).

VEGF, in particular, appears to play a pivotal role in human RA. Increased levels of VEGF have been found in both synovial fluid and serum of RA patients. In addition, these levels correlation with the clinical severity of human RA and the degree of joint destruction (Koch et al. 1994; Fava et al., 1994; Nagashima et al., 1995; Ballara et al., 2001; Hirchon et al., 2002). Immunohistochemical and in situ hybridization studies of synovial tissues have shown that VEGF is strongly expressed by subsynovial macrophages, fibroblasts, surrounding microvessels, and synovial lining cells. (Ballara et al., 2001; Scola et al., 2001; Jackson et al., 1997). VEGF expression in diseased joints begins early and persists throughout the course of the disease (Ballara et al., 2001; Weber et al., 2002). Together these data support the hypothesis that VEGF plays a unique role in mediating angiogenesis in RA and that blocking VEGF's activity in vivo could be of therapeutic benefit for RA patients.

Accordingly, any of the conjugates or variants of sFlt-1 described herein, as well as compositions comprising such conjugates or variants of sFlt-1, can be used in a method to treat RA or reduce or ameliorate one more symptoms thereof.

Non-Limiting Example of VEGF Inhibitors for the Treatment of Cancer

A promising approach for cancer therapeutics also targets angiogenesis, which is a prerequisite for tumor growth and metastasis (see review by Zetter, 1998). Solid tumors are incapable of growth beyond a certain critical diameter of a few millimeters without new blood vessels supplying them with nutrients and oxygen. Recent work has demonstrated that cancer cells overproduce potent angiogenic factors such as VEGF and basic fibroblast growth factor (bFGH) that stimulate this new growth (Relf et al., 1997). Cancers with higher densities of blood vessels and increased levels of angiogenic factors are more likely to spread and have poorer clinical outcomes (Weidner et al., 1991). Preliminary animal studies have assessed the activities of various angiogenesis inhibitors and have shown them to be highly effective in reducing primary tumor growth and retarding metastases (Singh et al., 1997; Herbst et al., 1998).

Angiogenesis inhibitors have several advantages over standard cancer therapies such as chemotherapy or ionizing radiation. First, anti-angiogenic agents target the capillary-making cells that are normal, genetically stable cells and should therefore, unlike tumor cells, be incapable of developing resistance. Minimal toxicity is expected as compared to standard cancer treatments that devastate normal cells, causing bone marrow suppression, loss of hair and nausea. Since the mechanism of angiogenesis inhibition differs from conventional therapies, the possibility of using several cancer drugs in combination may prove more effective than either agent separately. Indeed, radiation therapy in conjunction with anti-angiogenesis agents improved tumor eradication without increasing deleterious effects (Mauceri et al., 1998). Lastly, depending on the side effects, anti-angiogenic drugs could be given prophylactically to individuals known to be at high risk for recurring or new tumors.

Accordingly, any of the conjugates or variants of sFlt-1 described herein, as well as compositions comprising such conjugates or variants of sFlt-1, can be used in a method to reduce angiogenesis, or to treat a disease or condition associated with excessive or abnormal angiogenesis (e.g., cancer), or to reduce or ameliorate one more symptoms thereof.

The following examples are provided for the purpose of illustration and are not intended to limit the scope of the present invention. Each publication or other reference disclosed below and elsewhere herein is incorporated herein by reference in its entirety.

EXAMPLES

Example 1

Cloning and Expression Of Human sFlt-1, Truncated Forms of sFlt-1, and Cysteine Muteins of sFLT-1 and their Truncated Forms Previous published reports showed that the soluble form of Flt-1 (sFlt-1(f1) containing 6 Ig-like domains, Mw=74, 800) expressed in mammalian cells exhibited VEGF inhibitory activity. In addition, based on previously published data, a truncated form of sFlt-1 containing domains 1-3 (sFlt-1(3), MW=35, 300) could be expressed in *E. coli* when fused to a histidine tag. Here we describe the cloning and expression of both the three-domain (sFlt-1(3)) and full length six-domain molecule (sFlt-1(f1)) in *E. coli*.

A PCR fragment encoding sFlt-1(3) was amplified from a single strand liver cDNA library (Clontech) using primers BB966 and BB968 (oligonucleotide sequences are shown in Table 1, below.) In order to obtain a substantial amount of PCR fragment for cloning, two rounds of amplification were required. The amplification conditions were: 95° C., 5 min; followed by 30 cycles of 94° C., 30 sec; 59° C., 30 sec; 72° C., 30 sec; followed by 72° C., 5 min; and finally 4° C. overnight. (When PCR conditions are not specified they are: 95° C., 5 min; followed by 25 cycles of [94° C., 30 sec; 55° C., 30 sec; 72° C., 30 sec]; followed by 72° C., 5 min; and finally 4° C. overnight.) After purifying the PCR fragment, it was digested with BamHI and EcoRI and cloned into similarly digested pUC19, yielding plasmid pBBT829. Aside from 2 silent mutations (i.e. 2 nucleotide differences from published Flt-1 sequences that did not alter the amino acid sequence of the Flt-1 protein), the sequence was identical to the published sequence of sFlt-1(3).

The BamHI-EcoRI fragment was transferred to BamHI-EcoRI digested pET21a+ (Novagen). This plasmid, named pBBT821, was transformed into the *E. coli* strain Rosetta (DE3) (Novagen), yielding the strain BOB1057. Expression of sFlt-1(3), fused at its amino-terminus to the "T7 tag," was achieved by growing BOB1057 to an absorbance at 600 nm (A600) of ~0.7, and inducing expression with 0.5 mM IPTG. Cells were harvested at 2 to 3 hrs after induction.

In order to express the sFlt-1 without the T7 tag, the 5' end of the gene was modified to include a translation coupler, as follows. First, a fragment of DNA encoding a translational coupler followed by Flt-1 residues 23-90 was constructed from synthetic oligonucleotides, as follows. BB1001 and BB1002 were mixed and annealed at 41° C., BB1003 and BB1004 were mixed and annealed at 50° C., and BB1005, BB1006, and BB1007 were mixed and annealed at 50° C. Each oligonucleotide mixture was PCR-amplified for 3 cycles. A mixture containing one microliter from each of these 20 μl reactions was amplified by PCR for 3 cycles at an annealing temperature of 41° C., at which time BB1007 and BB1012 were added, and 20 cycles of PCR amplification were performed with an annealing temperature of 57° C. The DNA fragment produced from this PCR was digested with BamHI and EcoRI and inserted into similarly digested pUC19, yielding the plasmid pBBT863. The sequence of this insert was found to be correct.

Plasmid pBBT829 (above), carrying the sFlt-1 gene, was digested with BamHI and EcoRI, and the ~1 kbp fragment was purified and inserted into similarly digested pUC18 and pBBT108 (pBBT108 is identical to pUC19 except that the PstI site was mutagenized and is no longer recognized by this restriction enzyme). The resulting plasmids are pBBT866 (the pUC18 derivative) and pBBT868 (the pBBT108 derivative). pBBT866 is the starting point for the "direct start" expression construct and pBBT868 is the starting point for the "translationally coupled" expression construct (see below).

The sFlt-1 fragment in pBBT863 was amplified by PCR using primers BB1014 and BB1007 to remove codons 23-26. The DNA fragment produced from this PCR was digested with BamHI and PstI, and ligated with similarly digested pBBT868, yielding plasmid pBBT882. The inserted fragment was sequenced and found to be correct.

pBBT882 was digested with BamHI and EcoRI and ligated with pET21a+digested with the same restriction enzymes and calf intestine alkaline phosphatase (CIP)-treated. The resulting pET21a+-derived plasmid, termed pBBT888, carries the gene for sFlt-1(3), preceded by a translational coupler sequence. This plasmid was transformed into Rosetta (DE3) to produce the strain BOB1157. Expression of wild type sFlt-1(3) was achieved by growing BOB1157 to an absorbance at 600 nm (A600) of ~0.7, and inducing expression with 0.5 mM IPTG. Cells were harvested at 2 to 3 hrs after induction.

An alternative expression construct, termed a "direct start," has an NdeI site at the 5' end of the gene. In this construct, the ATG sequence within the NdeI site serves as the start codon for translation of the gene. To prepare this construct, the Flt-1 fragment in pBBT863 was amplified by PCR using primers BB1015 and BB1007 to remove the translational coupler and codons 23-26. The DNA fragment produced from this PCR was digested with NdeI and PstI, and ligated with similarly digested pBBT866 (described above), yielding plasmid pBBT881. The inserted fragment was sequenced and found to be correct.

pBBT881 was digested with NdeI and EcoRI and ligated with pET21a+ digested with the same restriction enzymes and calf intestine alkaline phosphatase (CIP)-treated. The resulting pET21a+ derived plasmid, termed pBBT887, carries the gene for sFlt-1(3). This plasmid was transformed into Rosetta (DE3) to produce the strain BOB1156. Expression of sFlt-1(3) was achieved by growing BOB1156 to an absorbance at 600 nm (A600) of ~0.7, and inducing expression with 0.5 mM IPTG. Cells were harvested at 2 to 3 hrs after induction.

A clone of sFlt-1(6) with the correct sequence was constructed by ligating the DNA fragment in pBBT829 (containing sFlt-1(3), above) to multiple fragments encoding sections of domains 4 through 6 (Flt-1(4-6)). PCR fragments encoding sFlt-1(4-6) were obtained by amplifying DNA from a single strand liver cDNA library (Clontech) using either primers BB980 and BB997, or primers BB980 and BB966. The PCR fragment obtained from primers BB980 and BB997 was gel purified and further amplified by PCR using primers BB967 and BB997. The resulting fragment was termed 967×997. The PCR fragment derived from primers BB980 and BB966 was gel purified and further amplified using primers BB967 and BB966. The resulting fragment was termed 967×966. The fragment 967×997 was digested with EcoRI and ligated with pUC19 digested with EcoRI and HincII. The plasmid derived from this cloning is pBBT830. The fragment 967×966 was digested with BamHI and EcoRI and ligated with similarly digested pUC19, yielding plasmid pBBT831. pBBT830 was sequenced and shown to be the same as the published sequence of sFlt-1 between the BsmI site at residues 332-333 and the NdeI site as residues 456-458, whereas the sequence of pBBT831 was found to contain a single silent mutation between the NdeI site and the gene's stop codon. The construction of the 6 domain sequence was done by isolating the ~370 bp BsmI/NdeI fragment from pBBT830, and the ~600 bp NdeI/EcoRI fragment from pBBT831, and ligating these two fragment with pBBT829 digested with BsmI and EcoRI. The resulting plasmid, pBBT851, encoding sFlt-1(f1), was found to have the sequence expected from the sequences of the DNA fragments used in its construction.

To express sFlt-1(f1) in *E. coli*, the plasmid pBBT851 was cut with BsmI and EcoRI, and the ~970 bp fragment was gel purified. This fragment was ligated with pBBT882 digested with the same enzymes. The resulting plasmid, pBBT904, was transformed into Rosetta (DE3) to produce the strain BOB1184. Expression of sFlt-1(f1) was achieved by growing BOB1184 to an absorbance at 600 nm (A600) of ~0.7, and inducing expression with 0.5 mM IPTG. Cells were harvested at 2 to 3 hrs after induction.

Cysteine muteins of sFlt-1(3) were generated by PCR using oligonucleotide mediated site-specific mutagenesis of the sFlt-1(3) gene (S. J. Scharf, 1990, R. Higuchi, 1990). For the two muteins G26C (i.e. the glycine at position 26 replaced by a cysteine) and H338C, the method of Scharf (which requires only one mutagenic oligonucleotide) was used. For the 4 muteins N100C, N164C, N196C, and N323C, the Higuchi method (requiring 2 mutagenic oligonucleotides) was employed.

For G26C, primers BB1018 and BB982 were used to amplify template pBBT872. The DNA fragment generated from the PCR reaction was digested with BamHI and BsrGI, and ligated with BamHI/BsrGI-digested and CIP-treated pBBT872. After confirming the sequence of the inserted fragment, the resulting plasmid, pBBT922, was digested with BamHI and EcoRI, and ligated with similarly digested and CIP-treated pET21a+.

For H338C, primers BB1027 and BB981 were used to amplify pBBT872. The DNA fragment generated from the PCR reaction was digested with MfeI and EcoRI, and ligated with Mfe/EcoRI-digested and CIP-treated pBBT872. After identifying a clone with a single fragment inserted in the correct orientation and confirming the sequence of the inserted fragment, the resulting plasmid was digested with BamHI and EcoRI, and ligated with similarly digested and CIP-treated pET21a+.

For N100C, primers BB1019 and BB982 were used to amplify pBBT872, producing a fragment containing the mutation and sequences downstream of the mutation (the "right" PCR product). Primers BB1020 and BB126 were used to amplify pBBT872, producing the "left" PCR product. The outside primers used in the splicing reaction were BB126 and BB982. The spliced PCR product was digested with BamHI and BsrGI, and ligated with similarly digested and CIP-treated pBBT872, producing the plasmid 872/100. After confirming that the sequence of the inserted fragment was correct, 872/100 was digested with KpnI and EcoRI and the 906 bp fragment was gel purified and ligated with similarly digested and CIP-treated pET21a+ to produce pBBT924.

For N164C, primers BB1021 and BB385 were used to amplify pBBT872, producing the "right" PCR product, and primers BB1022 and BB126 were used on the same template to produce the "left" PCR product. The outside primers used in the splicing reaction were BB126 and BB385. The spliced PCR product was digested with BsrGI and MfeI, and ligated with similarly digested and CIP-treated pBBT872, producing the plasmid 872/164. After confirming that the sequence of the inserted fragment was correct, 872/164 was digested with KpnI and EcoRI and the 906 bp fragment was gel purified and ligated with similarly digested and CIP-treated pET21a+ to produce pBBT924.

For N196C, primers BB1023 and BB385 were used to amplify pBBT872, producing the "right" PCR product, and primers BB1024 and BB126 were used to produce the "left" PCR product. The outside primers used in the splicing reaction were BB126 and BB385. The spliced PCR product was digested with BsrGI and MfeI, and ligated with similarly digested and CIP-treated pBBT872, producing the plasmid 872/196. After confirming that the sequence of the inserted fragment was correct, 872/164 was digested with KpnI and EcoRI and the 906 bp fragment was gel purified and ligated with similarly digested and CIP-treated pET21a+ to produce pBBT924.

For N323C, primers BB1025 and BB125 were used to amplify pBBT872, producing the "right" PCR product, and primers BB1026 and BB981 were used to produce the "left" PCR product. The outside primers used in the splicing reaction were BB125 and BB981. The spliced PCR product was digested with MfeI and NdeI, and ligated with similarly digested and CIP-treated pBBT872, producing the plasmid 872/323. After confirming that the sequence of the inserted fragment (between the MfeI and EcoRI sites) was correct, 872/323 was digested with KpnI and EcoRI and the 906 bp fragment was gel purified and ligated with similarly digested and CIP-treated pET21a+ to produce pBBT924.

For D31C, primers BB1051 and BB982 were used to amplify pBBT882, producing the "right" PCR product, and primers BB1052 and BB126 were used to produce the "left" PCR product. The outside primers used in the splicing reaction were BB126 and BB982. The spliced PCR product was digested with BamHI and BsrGI, and ligated with similarly digested and CIP-treated pBBT882, producing the plasmid 882/31. After confirming that the sequence of the inserted fragment was correct, 882/31 was digested with BamHI and EcoRI and the 966 bp fragment was gel purified and ligated with similarly digested and CIP-treated pET21a+ to produce pET-Flt D31C.

Cysteine muteins of sFlt-1 were expressed in *E. coli* using the same methods as were used to express the wild type protein.

TABLE 1

Synthetic Oligonucleotides

| Name | Sequence |
|---|---|
| BB125 | 5'CTATGCGGCATCAGAGCAGAT (SEQ ID NO:3) |
| BB126 | 5'TGTGGAATTGTGAGCGGATAAC (SEQ ID NO:4) |
| BB385 | 5'TGCTGCAAGGCGATTAAGTTG (SEQ ID NO:5) |
| BB966 | 5'CGCGGATCCTCTAGTTCAGGTTCAAAATTAAAAGATCC (SEQ ID NO:6) |
| BB967 | 5'CCGGAATTCTTATCTGATTGTAATTTCTTTCTTCTG (SEQ ID NO:7) |
| BB968 | 5'CCGGAATTCTTAATGTTTCACAGTGATGAATGCTTTATC (SEQ ID NO:8) |
| BB980 | 5'GTGCTCACCTCTGATTGTAATTTCTTTC (SEQ ID NO:9) |
| BB981 | 5'CCACTTGACACTTTGATCCCT (SEQ ID NO:10) |
| BB982 | 5'ATTGGTTTGTCGATGTGTGAG (SEQ ID NO:11) |
| BB997 | 5'TTCAAATCTGTTAACACCTCAGTGC (SEQ ID NO:12) |
| BB1001 | 5'GAGGATGATTAAATGTCTAGTTCAGGTTCAAAACTGAAAGAT (SEQ ID NO:13) |
| BB1002 | 5'GATGTGCTGGGTACCTTTTAAGCTCAGTTCAGGATCTTTCAGTTTTGAACCTGAACTAGA (SEQ ID NO:14) |
| BB1003 | 5'GGTACCCAGCACATCATGCAAGCAGGCCAGACACTGCATCTCCAATGCCGTGGG (SEQ ID NO:15) |
| BB1004 | 5'CACCATTTCAGGCAAAGACCATTTATGGGCTGCTTCCCCACGGCATTGGAGATG (SEQ ID NO:16) |
| BB1005 | 5'CTTTGCCTGAAATGGTGAGTAAGGAAAGCGAACGTCTGAGCATCACTAAATCTGCC (SEQ ID NO:17) |
| BB1006 | 5'TAAAGTACTGCAGAATTGTTTGCCATTACGACCACAGGCAGATTTAGTGATGCTCAG (SEQ ID NO:18) |
| BB1007 | 5'GCGAATTCTAAAGTACTGCAGAATTGTTTGCC (SEQ ID NO:19) |
| BB1012 | 5'CGCGGATCCATCTTGGAGGATGATTAAATGTCTAGTTCAGGTTCAAAACTG (SEQ ID NO:20) |
| BB1014 | 5'CGCGGATCCATCTTGGAGGATGATTAAATGTCTAAACTGAAAGATCCTGAACTGAG (SEQ ID NO:21) |

TABLE 1-continued

| Synthetic Oligonucleotides | |
|---|---|
| Name | Sequence |
| BB1015 | 5'CGCCATATGTCTAAACTGAAAGATCCTGAACTGAG (SEQ ID NO:22) |
| BB1018 | 5'CGCGGATCCATCTTGGAGGATGATTAAATGTGTTCTAAACTGAAAGATC (SEQ ID NO:23) |
| BB1019 | 5'GAACACAGCCCAAGCATGCCACACTGGCTTC (SEQ ID NO:24) |
| BB1020 | 5'GAAGCCAGTGTGGCATGCTTGGGCTGTGTTC (SEQ iD NO:25) |
| BB1021 | 5'GGTTACGTCGCCATGCATCACTGTTACTTTAAA (SEQ ID NO:26) |
| BB1022 | 5'TTTAAAGTAACAGTGATGCATGGCGACGTAACC (SEQ ID NO:27) |
| BB1023 | 5'GGCTTCATCATATCATGCGCAACGTACAAAGA (SEQ ID NO:28) |
| BB1024 | 5'TCTTTGTACGTTGCGCATGATATGATGAAGCC (SEQ ID NO:29) |
| BB1025 | 5'TCATTCAAATCTGTTTGCACCTCAGTGCAT (SEQ ID NO:30) |
| BB1026 | 5'ATGCACTGAGGTGCAAACAGATTTGAATGA (SEQ ID NO:31) |
| BB1027 | 5'CGCGAATTCTTAGCATTTCACAGTGATGAATGC (SEQ ID NO:32) |
| BB1051 | 5'GATTAAATGTCTAAACTGAAATGTCCGGAACTGAGCTTAAAAGG (SEQ ID NO:33) |
| BB1052 | 5'CCTTTTAAGCTCAGTTCCGGACATTTCAGTTTAGACATTTAATC (SEQ ID NO:34) |

Example 2

Eukaryotic Expression of Recombinant sFlt-1 and the sFlt-1 Cysteine Variants sFlt-1, sFlt-1 cysteine muteins and their various truncated forms can also be expressed as intracellular or secreted proteins in eukaryotic cells such as yeast, insect cells or mammalian cells. Vectors for expressing the proteins and methods for performing such experiments are described in catalogues from various commercial supply companies such as Invitrogen, Inc., Stratagene, Inc. and CloneTech, Inc. sFlt-1 variants can also be produced in transgenic animals.

Example 3

Bench Scale Preparation of Wild Type sFlt-1 and the sFlt-1 Variant in *E. coli*

A. Expression

The strains containing wild type sFlt-1 or sFlt-1 variants were grown overnight in Luria Broth (LB media) containing 100 μg/ml ampicillan, 25 μg/ml chloramphenicol at 37° C. in roll tubes. Saturated overnight cultures were diluted to ~0.025 OD at $A_{600}$ in the same media and incubated at 37° C. in shake flasks. Typically a 400 ml culture was grown in a 2 L shake flask. When culture ODs reached ~0.3-0.5, IPTG was added to a final concentration of 0.5 mM to induce expression of human sFlt-1 proteins. The cells were harvested by centrifugation, 3 hours post induction and frozen at −20° C.

B. Cell Break Conditions

Cell pellets were thawed and treated with 10 ml of B-PER™ bacterial protein extraction reagent according to the manufacturer's (Pierce) protocols. The insoluble material, which contains the bulk of the sFlt-1 protein, was recovered by centrifugation and resuspended in 10 ml B-PER™. This mixture was next treated with lysozyme (200 μg/ml) for 10 min to further disrupt the cell walls, followed by $MgCl_2$ (10 mM final concentration) and protease-free DNAse (2 μg/ml). Insoluble sFlt-1 protein was collected by centrifugation and washed by resuspension in water and recentrifugation, to remove most of the solubilized cell debris. Alternatively cell pellets can be broken by high-pressure homogenization using a French press for small-scale preparations or a Niro Panda or similar instrument for larger scale preparations. The insoluble sFlt-1 can be recovered by centrifugation or filtration.

C. Refold Optimizations Studies

A variety of conditions commonly used to refold proteins were tested in an experimental matrix format with wild type sFlt-1, the cysteine variants, and truncated forms of the cysteine variants. Solubilization reagents tested included urea (6-8 M) and guanidine (6-8 M) in the presence of a reducing agents (dithiothreitol, cysteine or cystamine 0-100 mM), and 20 mM Tris, base. For the renaturation step, the solubilizations were diluted 20 fold with a buffered solution which contained one or more of the following additives: glycerol (0-50%), arginine (0-0.5 M), Tween 20 (0-0.1%) guanidine (0-1 M), urea (0-2 M), copper sulfate (0-40 μM), cystamine (0-5 mM), cystine (0-5 mM), and EDTA (0-5 mM). Suitable buffers for the solubilization and renaturation steps include but are not limited to Tris, BisTris, phosphate and glycine at concentrations between 10 to 100 mM with pH ranging from 6-10. Alternatively the solubilization mixture was dialyzed against the renaturation buffer rather than diluted with the renaturation buffer. The refolds were left at 4° C. and analyzed by C4 Reversed Phase HPLC for up to 6 days to determine the optimum conditions.

The greatest yield of refolded soluble sFlt-1 resulted when the insoluble material recovered from the detergent cell break was dissolved in 6 M guanadine, 100 mM dithiothreitol in 50 mM sodium phosphate, pH 6.5. This mixture was stirred for 2 hours at room temperature before being diluted 20 fold into the renaturation solution consisting of 0.5 M arginine, 40 μM copper sulfate, 33 mM cystamine, 7 mM glycine, 1 mM EDTA, and 20 mM Tris, pH 8.0. This refold mixture was allowed to sit at 4° C. for up to 6 days.

D. Purification of the sFlt-1 Proteins to Homogeneity

Each refold (400 ml) was clarified by centrifugation before being diluted 3.5-fold with buffer A (20 mM Tris, 10% glycerol, 0.05% Tween 20, pH 8). The mixture was next loaded onto a 10 ml S-Sepharose column (GE BioSciences) equilibrated in Buffer A. The column was washed with 8 column volumes of 75% Buffer A: 25% Buffer B (20 mM Tris, 10% glycerol, 0.05% Tween 20, 1 M NaCl, pH 8.0. The remaining bound proteins were eluted with a linear salt gradient from 25%-100% Buffer B (20 column volumes). The S-Sepharose fractions were analyzed by SDS-PAGE. Those fractions that contained predominantly sFlt-1 protein were pooled.

Further purification was achieved by hydrophobic chromatography. The S-Sepharose pool was adjusted to a NaCl concentration of 3 M before being loaded on to a 1 mL Phenyl-Sepharose column (GE Biosciences), previously equilibrated in 20 mM Tris, pH 8.0, 10% glycerol, 0.05% Tween 20, 3 M NaCl. The column was eluted with a reverse salt gradient salt gradient form 3-0 M NaCl over 20 column volumes. Fractions were analyzed by SDS-PAGE. Fractions with substantially pure sFlt-1 were pooled and frozen. Protein concentrations were measured using a Bradford protein assay. Between 1-6 mgs of purified sFlt-1 protein (depending on the construct) were typically recovered from a 400 ml shake flask culture.

Example 4

C4 HPLC Assay for Characterization of the Wild Type and Flt-1 Mutants

A Reversed Phase (C4) HPLC method was developed for the purpose of evaluating refold yields and the final purity of the recombinant sFlt-1 and the sFlt-1 variants. A 50 μl aliquot of sample is applied to a C4 Vydac (214TP5415) (or similar C4 HPLC column) previously equilibrated in 80% Buffer A (water+0.1% trifluoroacetic acid (TFA): 10% Buffer B (acetonitrile+0.1% TFA). The column is eluted with a 15 minute linear gradient from 90% Buffer A to 10% Buffer A. Absorbance is monitored at 215 nm. A Beckman System Gold HPLC can be used for these experiments. The sFlt-1 proteins typically elute between 8-10 minutes depending on the mutation and construct.

Example 5

Amine PEGylation of sFlt-1 and Variants

Wild type sFlt-1 or sFlt-1 variants such as the truncated forms described previously can also be PEGylated using amine reactive PEG reagents. Because the water hydroxyl anion of the aqueous buffer competes with the primary amines, an excess of active PEG is usually needed, on the order of 2× to 100× depending on the protein's reactivity. The predominant site(s) of PEGylation can be controlled based on the pH of the buffer. Generally, at pH values above 8.0, the epsilon-NH3 groups react first whereas at approximated pH 5-7, alpha-NH2 is the most reactive.

For N-terminal PEGylation, sFlt-1 is diluted into a buffer that has sufficient capacity to maintain the pH of the reaction between 5-7. Buffers containing primary amines such as Tris should be avoided. The protein's concentration can be on the order of 0.01 mg-50 mg/mL. PEG is added on the order of 2- to 100-fold excess, preferably 2- to 10-fold excess. The reaction is allow to sit overnight at 4° C. or until the reaction is considered complete. The PEGylated protein is separated from the non-PEGylated protein and the PEG reagents by column chromatography using ion exchange, hydrophobic interaction, or size exclusion chromatography. Chromatography can also be used to separate the PEGylated isoforms of the proteins that vary by the location and/or the number of PEGs attached. The proteins can be visualized by UV absorbance at 280 nm whereas the PEG molecules can be identified by iodine assay (Sims et al., 1980).

For non-specific amine PEGylation the above reaction is run at a pH greater than 8. The number of attachments desired in the final product can be controlled by the amount of excess PEG reagent added and the time that the reaction is allowed to proceed.

Example 6

Thiol Specific PEGylation of sFlt-1 and Variants of sFlt-1

A. PEGylation Optimization Reactions

One μg aliquots of purified a Flt-1 cysteine analog (for example, sFlt-1 variants containing cysteine substitutions at a glycosylation site such as N100C, N164 C, N196C, and N323C or at a surface exposed site such as G26C or H338C were incubated with increasing concentrations of a reducing agent such as TCEP [Tris(2-carboxyethyl)phosphine-HCl] at room temperature in 100 mM Tris, pH 8.5 in the presence of varying amounts of excess 5 kDa maleimide-PEG. After 2 hr, the reactions were immediately analyzed by non-reducing SDS-PAGE. The amounts of TCEP and PEG reagent that yielded significant amounts of monoPEGylated sFlt-1 cysteine mutein, without modifying wild type sFlt-1 were chosen as optimal. TCEP was used as the reducing agent for these experiments because it does not interfere with the PEGylation reaction. Alternatively, dithiothreitol can be used as the reducing agent and then subsequently removed by dialysis or chromatography before adding the PEG reagent. The titration experiments indicated that 4 additions (at time 0, 30 min, 1 hr and 1.5 hr) of equal molar amounts of TCEP and 20 kDa maleimide PEG relative the protein gave up to 90% monoPEGylated protein without detectable di or tri-PEGylated protein, or modification of wild type sFlt-1.

B. Purification of PEGylated sFlt-1

The sFlt-1 cysteine mutein (0.5 mg) was diluted in 100 mM Tris, pH 8 to a final concentration of 50 μg/ml. Equal molar amounts of 20 kDa maleimide-PEG (Nektar) and TCEP were added at 30 min intervals for a total reaction time of 2 hours. The mixture was diluted with an equal volume of the Cu IMAC column Buffer A (20 mM sodium phosphate, 10% glycerol, 0.05% Tween 20, 0.2 M NaCl, pH 8.0). The PEGylated protein was purified using a 1 ml Chelating-Sepharose column charged with copper chloride and equilibrated Cu IMAC column Buffer A. PEGylated sFlt-1 was eluted with a gradient of 0-100% Buffer B (Buffer A+75 mM imidazole) over 20 column volumes. The fractions were analyzed by SDS-PAGE. Fractions containing purified PEG-Cys-Flt-1 were pooled and analyzed by the Bradford assay to determine the protein concentration.

Example 7

Method for Measuring the Bioactivities of Purified Wild Type sFlt-1 and the sFlt-1 Mutants Human Vein Umbilical Endothelial Cells (HUVEC) can be obtained from Cascade Biologics. The cells are grown to approximately 70% confluence in Medium 200 containing Low Serum Growth Supplement (LSGS) from Cascade Biologics at 37° C. in a humidified 5% $CO_2$ tissue culture incubator. Cells were harvested, resuspended at a concentration of $1\times10^6$/ml in Medium 200 with LSGS+10% DMSO, and aliquotted in 1 ml volumes. Aliquotted cells were frozen at −80° C. for approximately 24 hours and subsequently transferred to liquid nitrogen for storage. Cells were considered to be at passage two at the time of storage.

For bioassays, cryopreserved cells were quickly thawed in a 37° C. water bath and cultures established at an approximate density of 2, 500 cells/$cm^2$ in Medium 200 containing LSGS. Cells were incubated at 37° C. in a humidified 5% CO2 incubator and allowed to reach 60-80% confluence. Cells were washed with Dulbecco's Phosphate Buffered Saline (Gibco Cat No. 14190-144) and harvested using Trypsin-EDTA (Gibco Cat. No. 25300-054) diluted two fold with DPBS. The trypsinization reaction was stopped with Medium 200 supplemented with 5% Fetal Bovine Serum (Hyclone Cat. No. SH30079.03). Cells were resuspended at a concentration of $1\times10^5$/ml in Medium 200 supplemented with 5% FBS (assay media). Recombinant Human Vascular Endothelial Growth Factor (rhVEGF) was obtained from Cells Sciences, Inc and diluted to 120 ng/ml in assay buffer. Twenty-five μl of VEGF was aliquoted per test well of a flat bottom 96 well tissue culture plate. Serial dilutions of the sFlt-1 protein samples to be tested were prepared in assay media and 25 μl was added to the test wells. Protein samples were assayed in triplicate. The plates were incubated at 37° C. in a humidified 5% $CO_2$ incubator for 1 hour. Fifty μl ($5\times10^3$ cells) of the cell suspension were added to the test wells and the plate returned to the incubator.

After 3 days the plates were developed using the colorimetric BrdU Cell Proliferation assay (Roche Applied Sciences) as described in the product instruction manual. The BrdU Cell Proliferation assay is a non-isotopic immunoassay for quantification of bromodeoxyuridine incorporation into newly synthesized DNA of actively proliferating cells. Briefly, 10 μl of the BrdU labeling solution is added to the test wells of the 96 well assay plate and incubated at 37° C. in a humidified 5% $CO_2$ incubator for 4 hours. Labeling media is removed by aspiration and the cells are allowed to air dry for 30 minutes. Two hundred μl of fixing solution are added to each well and incubated at room temperature for 45 minutes. The fixing solution is removed by aspiration and replaced with 100 μl of anti-BrdU-POD antibody solution and incubated at 37° C. in a humidified 5% $CO_2$ incubator for 90 minutes. The antibody solution is removed and the wells washed 3 times with 200 μl washing buffer per wash. One hundred μl of TMB-substrate solution are added to each test well and the reaction allowed to develop at room temperature until sufficient for photometric detection. The reaction is stopped by the addition of 25 μl of 1M $H_2SO_4$ and the plates read at a test wavelength of 450 nm and a reference wavelength of 630 nm using a microplate reader.

Various forms of the sFlt-1 including truncated, cysteine analogs, and PEGylated forms of sFlt-1 can be evaluated using BrdU Cell Proliferation assay described above. Average $EC_{50}$ values for several sFlt-1 variants are shown in Table II.

TABLE II

Bioactivity Data for sFlt-1 variants and PEGylated sFlt-1 variants

| sFlt-1 Variant | Ave $Ec_{50's}$ (ng/ml) | PEGylated sFlt-1 Variant | Ave $Ec_{50's}$ (ng/ml) |
|---|---|---|---|
| Wild type sFlt-1(fl) | 76 | — | — |
| Wild type sFlt-1(3) | 36 | — | — |
| sFlt-1(3) G26C | 43 | 20 kDa-Cys-Flt-1(3) G26C | 54 |
| sFlt-1(3) D31C | 60 | 20 kDa-Cys-Flt-1(3) D31C | 80 |
| sFlt-1(3) N100C | 53 | 20 kDa-Cys-Flt-1(3) N100C | 66 |
| sFlt-1(3) N164C | 103 | 20 kDa-Cys-Flt-1(3) N164C | 75 |
| sFlt-1(3) N196C | 88 | 20 kDa-Cys-Flt-1(3) N196C | 59 |
| sFlt-1(3) N323C | 32 | 20 kDa-Cys-Flt-1(3) N323C | 40 |
| sFlt-1(3) H338C | 55 | 20 kDa-Cys-Flt-1(3) H338C | 19 |

Example 8

Preliminary Pharmacokinetic Experiments to Demonstrate Increased Circulating Half-Lives of PEG-Cys-sFlt-1 Relative to unPEGylated sFlt-1 Proteins A Pharmacokinetic (PK) experiment can be used to determine the circulating half-lives of PEGylated forms of sFlt-1 versus unPEGylated sFlt-1. Rats (3/group) are given a single intravenous (IV) (100 μg/kg) of wild type sFlt-1, 20 kDa or 40 kDa PEG-Cys-Flt-1(3). Blood samples are drawn over the course of 96 hours and frozen. A commercially available sFlt-1 ELISA kit (R&D systems) can be used to measure serum levels. It should be noted that the addition of the PEG linker can significantly block an antibody's ability to detect sFlt-1. Accordingly, the final values determined by the ELISA kit are adjusted for the decrease in signal as a result of the PEG moiety. Alternatively, quantitative Westerns blots can be run to determine serum levels.

As expected, a significant improvement in the circulating half-life of sFlt-1 was observed upon addition of a PEG moiety. Terminal pharmacokinetic parameters were calculated using WinNonlan software and non-compartmental analysis. The circulating half-lives were calculated to be 1.2 hr for wild type sFlt-1, 3.9 hr for 20 kDa PEGylated sFlt-1 (H338C) and 6.4 hr for 40 kDa PEGylated sFlt-1 (HCC8C).

Example 9

Evaluation of PEGylated sFlt-1's In Vivo Activity in Rheumatoid Arthritis Models The relative efficacies of the PEGylated sFlt-1 variants can be evaluated in a murine collagen induced arthritis (CIA) animal model. Murine CIA displays many of the hallmarks of human RA. CIA is induced in susceptible strains of mice by immunization with bovine collagen type II in complete Freund's adjuvant. The development of CIA is thought to depend on T cells, and disease susceptibility is linked to the MHC region. Following T cell activation an inflammatory cascade involving T cells, macrophages/monocytes, B cells, and activated synoviocytes, is triggered. The different leucocytes and synovial cells produce a complex array of cytokines and other soluble mediators, such as matrix metalloproteinases (MMP), that are thought to contribute to pannus formation, cartilage destruction and bone erosion. The relevance of this model has also been demonstrated using an anti-TNF antibody that was able to ameliorate CIA (Willams et al., 1992) and subsequently has proven to be clinical effective for the treatment of human RA (Maini et al., 1999).

Induction and Assessment of Collagen Induced Arthritis

Ten-week-old, inbred, male DBA/1 ($H\text{-}2^q$) mice (Harlan) receive a single intradermal injection of 100 μl bovine type II collagen emulsified in complete Freund's adjuvant (Difco, Detroit, Mich., USA) at the base of the tail. The first clinical signs of arthritis, as assessed by edema and/or erythema involving any of the paws, typically appear between days 14 and 28 after immunization, with a mean onset of arthritis at day 21 after immunization. Mice are monitored daily and each limb given a clinical score as follows: 0, normal paws and no clinical features of inflammation; 1, slight edema or erythema; 1.5, edema and erythema involving at least some digits; 2, frank edema/erythema involving the entire paw; and 2.5, pronounced edema and erythema leading to incapacitated limb mobility. Each limb is graded in this manner, giving a maximum possible score of 10 per mouse. All hind paws are measured daily to record the degree of paw thickness, using a fine engineer's caliper. The mice are humanely euthanized on day 10 of disease. Data are expressed as mean (±SEM) clinical score or paw thickness.

In Vitro Administration of Wild Type sFlt-1 or sFlt-1 Variants and PEGylated sFlt-1 Variants In order to assess the effect of sFlt-1 on established CIA, treatment is commenced from the first day of the onset of the clinical symptoms of arthritis, which is considered to be the day when the first visible signs of erythema and/or edema are observed in any of the limbs. Mice are randomly selected and assigned to one of the following groups: no treatment, vehicle (equal volume of PBS, pH 7.2), sFlt-1 and PEG-Cys-sFlt-1. The route of delivery can be intravenous or subcutaneous, and can be based on previous rat PK studies. Data from rats generally can be extrapolated to mice because PK parameters are proportional to body weight (Mahmood, 1998). Treatments are given over a period of 10 days. Assessments of clinical score and paw thickness are performed by an observer who is unaware of the treatment group to which the animals have been assigned. Histological assessments can also be performed on the hind feet after death with sections being screened for changes in joint architecture.

Example 10

Evaluation of PEGylated sFlt-1's In Vivo Activity in Animal Tumor Models

A. Lewis Lung Animal Model to Test Efficacy of PEG-Cys-Flt-1.

The efficacy of PEG-Cys-Flt-1 can be tested in the Lewis lung carcinoma mouse model. Mice are injected in the proximal midline of the subcutaneous dorsa with $1\times10^6$ cells (Lewis Lung carcinoma) in 0.1 mL of saline. When the tumors are around 600-800 $mm^3$ in size, the mice are killed and the tumors surgically removed. A suspension of the tumor cells in 0.9% saline can be made by passage of viable tumor tissue through a sieve and a series of sequentially smaller hypodermic needles. The final concentration of the tumor cells is adjusted to $1\times10^7$ cells/ml. The Lewis lung carcinoma cells are next injected ($2\times10^6$ cells) into the sc dorsa at the proximal midline of C57BL/6 mice. When the tumors attain a volume of 90-100 $mm^3$, the animals begin drug therapy. Groups of 6 mice will receive daily (ED), every other day (EOD) or every third day (ETD) subcutaneous injections unmodified sFlt-1 or PEG-Cys-Flt-1 or placebo for 14 days. Tumor growth is monitored by periodic caliper measurements. Tumor volume can be calculated by the following formula ($mm^3=(a\times b^2)/2$, where a is length in mm and b is width in mm. Statistical significance between the control and treated groups is determined by Student's t test. The experiments are terminated when tumors in control groups reach 2.0 cm in diameter or induced morbidity is observed. The timing of the injections and the preferred PEG-Cys-Flt-1 protein can be determined by the results of the rat PK experiments described above.

B. Evaluation of the Efficacy of PEG-Cys-Flt-1 in the MDA-MB-435 Xenograft Animal Model.

The MDA-MB-435 tumor model can be used to evaluate the inhibitory effects of a polymer modified Flt-1 protein on the growth of primary tumors resulting from the implantation of adenocarcinoma cells in female athymic nude mice. Five to six week old female BALB-c nu/nu mice can be used for this study. Animals are allowed to acclimate for a period of approximately one week prior to study commencement. The weight of each mouse is determined and recorded at 3-4 day intervals. On the first day of the study (day 0), each of the initial 30 mice is implanted with $1.0\times10^6$ MDA-MB-435 adenocarcinoma cells into the mammary fat pad (delivered in 0.1 ml of PBS). Tumors are allowed to develop for approximately 6 days, at which time 21 mice are selected based on similar tumor size and divided into 3 treatment groups of 7 animals each. The growth of the tumors is monitored using twice weekly caliper measurements. Once daily, every other day or every third day dosing is continued for a period of 21 days, after which time the animals were euthanized and the tumors removed and weighed.

Histological Analysis of Blood Vessel Density

The vascularity of excised tumors at the termination of study can be measured by CD-31 immunostaining. CD-31 is an endothelial cell marker commonly used to measure angiogenesis. Tumors are harvested and placed into 10% neutral buffered formalin for histopathologic analysis. After 24 hours they were transferred to 70% alcohol. Next they are processed and embedded into paraffin. Two 4 micron sections are cut. One section is stained with a routine morphological stain, Hematoxylin and Eosin. The other section is stained with an antibody against CD-31, an endothelial cell marker as described below.

Endothelial cells can be immunohistochemically stained with polyclonal goat anti-mouse PECAM-1, Clone M-20 (Santa Cruz Biotechnology, Santa Cruz, Calif.). A pretreatment of heat-induced-epitope retrieval in 10 mmol/L citrate buffer, pH 6.0 is utilized for the CD-31 antibody prior to the primary antibody incubation. Endogenous peroxidase is inhibited by incubation in 3% $H_2O_2$. Nonspecific staining can be blocked with DAKO Protein Block Serum-Free (DakoCytomation, Carpinteria, Calif.). After incubation with primary antibody, the tissue sections are sequentially incubated with biotinylated rabbit anti-goat immunoglobulins (Vector Laboratories, Burlington, Calif.), and then additionally treated with Dako Envision+ Rabbit System Labeled Polymer and HRP (DakoCytomation, Carpinteria, Calif.). Staining can be developed with Liquid DAB+ (DakoCytomation, Carpinteria, Calif.) and counterstained with Hematoxylin.

Tumor vascularization can be evaluated by utilizing the CD-31 immunohistochemical stain at a magnification of 200× on a Zeiss Axioskop 2 microscope. Concentration of vascular staining for all the tumors is examined and the highest concentration being rated 3+ and the lowest as 1+ (allowing that 0 indicates no staining). The remaining tumors are evaluated for the entire tumor and assigned values according to this standard as 0, 1+, 2+ or 3+. Subsequently, the number of vessels are counted by examining 5 fields per tumor at 200×. A digital image can be captured for each field using a Zeiss Axiocam HR Digital Camera and Axiovision software to count the number of CD31 positive vessels, capillaries and microvessels (Weidner et al., 1991; Restucci et al., 2000).

Necrosis is calculated at low magnification by an estimation of the percent of the tumor that is necrotic as follows: The entire tumor is scanned at a magnification of 40× on a Zeiss Axioskop 2 microscope for all of the tumors. The percentage of tumor that was necrotic is visually assessed.

REFERENCES

Abuchowski, A., Kazo, G. M., Verhoest, C. R., Van Es, T., Kafkewitz, D., Nucci, M. L., Viau, A. T. and Davis, F. F. (1984) Cancer Biochem. Biophys. 7: 175-186. Cancer therapy with chemically modified enzymes: antitumor properties of polyethylene glycol-asparaginase.

Arsenault, A L, Lhotak S, Hunter W L, Banquerigo M L, Bralin E (1998) Clin Immunol Immunopathol 1998, 86:280-289. Taxol involution of collagen-induced arthritis: ultrastructural correlation with the inhibition of synovitis and neovascularization.

Bailon P, Palleroni A, Schaffer C A, Spence C L, Fung W J, Porter J E, Ehrlich G K, Pan W, Xu Z X, Modi M W, Farid A, Berthold W, Graves M. (2001) Bioconjug Chem. 12(2): 195-202. Rational design of a potent, long-lasting form of interferon: a 40 kDa branched polyethylene glycol-conjugated interferon alpha-2a for the treatment of hepatitis C.

Ballara, S., Taylor, P. Reusch, D. Marme, D. Feldmann, M., Maini, R. and Paleolog, E. (2001) Arthritis Rheum. 44: 2055. Raised serum vascular endothelial growth factor levels are associated with destructive change in inflammatory arthritis.

Barleon, B., Siemester, G., Martiny-Baron, G., Weindel, K., Herzog, C. and D. Marme (1997) Cancer Res. 57: 5421-5425. Vascular endothelial growth factor up-regulates its receptor fms-like tyrosine kinase 1 (Flt-1) and a soluble variant of sFlt-1 in human vascular endothelial cells.

Cunningham, B. C., Ultsch, M., de Vos, A. M., Mulkerrin, M. G., Clauser, K. R. and Wells, J. A. (1991) Science 254: 821-825. Dimerization of the extracellular domain of the human growth hormone receptor by a single hormone molecule.

Davis-Smith, T. Chen, H. Park, J. Presta, L. G. and Ferrara, N. (1996) EMBO J 15, 4919-4927. The second Immunoglobulin-like domain of the VEGF tyrosine kinase receptor sFlt-1 determines ligand binding and may initiate a signal transduction cascade.

Davis-Smith, T., Presta, L. F., and Ferrara, N. (1998) J. Biol. Chem. 273: 3216-3222. Mapping the charged residues in the second immunoglobulin-like domain of the vascular endothelial growth factor/placenta growth factor receptor sFlt-1 but not to Flk-1/KDR.

de Bandt M, Grossin M, Weber A J, Chopin M, Elbim C, Pla M, Gougerot-Pocidalo M A, Gaudry M (2003) Arthritis Rheum, 43:2056-2063. Suppression of arthritis and protection from bone destruction by treatment with TNP-470/AGM-1470 in a transgenic mouse model of rheumatoid arthritis.

Deiters A, Cropp T A, Summerer D, Mukherji M, Schultz P G. (2004) Bioorg Med Chem. Lett. 14(23):5743-5745 Site-specific PEGylation of proteins containing unnatural amino acids.

Delgado, C. Francis, G E, and Derek (1992) Critical Rev Ther Drug Carrier Sys 9:249-304. The uses and properties of PEG-linked proteins.

Fava, R. Olsen N. Spencer-green, K. Yeo, B. Berse, R. Jackman, D., Senger, H., Dvorak, H. and Brown. L. (1994) J. Exp. Med. 180:341-346. Vascular permeability factor/endothelial growth factor (VPE/VEGF): accumulation and expression in human synovial fluids and rheumatoid synovial tissue.

Fee, C. (2003) Biotech and Bioeng. 82:200-206. Size-exclusion reaction chromatography: A new technique for protein PEGylation.

Foser S, Schacher A, Weyer K A, Brugger D, Dietel E, Marti S, Schreitmuller T. (2003) Protein Expr Purif. 30(1):78-87. Isolation, structural characterization, and antiviral activity of positional isomers of monopegylated interferon alpha-2a (PEGASYS).

Gerber, H., Kowalski, J., Sherman, D., Eberhard, D, and Ferrara, N. (2000) Cancer Res. 60:6253-6258. Complete inhibition of Rhabdomyosarcoma xenograft growth and Neovascularization requires blockage of both tumor and host vascular endothelial growth factor.

Harris, J. M. and Chess, R. B. (2003) Nat Rev. Drug Discov 2:214-221. Effect of PEGylation on pharmaceuticals.

Herbst, R. S., Takeuchi, H. and Teicher, B. A. (1998) Cancer Chemother. Pharmacol. 41:497-504. Paclitaxel/carboplatin administration along with antiangiogenic therapy in non-small-cell lung and breast carcinoma models.

Higuchi, R. in "PCR Protocols" (MA Innis, D H Gelfand, J J Sninsky, & T J White, eds.) Academic Press (1990) pp. 177-83 "Recombinant PCR"

Hiratsuka, S., Minowa, O., Kuno, J., Noda, T. and Shibuya, M. (1998) Proc. Natl. Acad. Sci. USA, 95: 9349-9354. Flt-1 lacking the tyrosine kinase domain is sufficient for normal development and angiogenesis in mice.

Hirchon, C., Wong, K., Ma, G., Reed, J. Lyttle, D., and El-Gabalawy, M. (2002) Arthritis Rheum. 46: 2587. Hypoxia-induced production of stromal cell-derived factor 1 and endothelial growth factor by synovial fibroblasts.

Hooftman, G. Herman, S., Schacht, E. (1996) J. Bioactive Compatible Polymer 11:135-139. PEGs with reactive end-groups II. Practical consideration for the preparation of protein-PEG conjugates.

Hornig, C. and Weich, H. (1999) Angiogenesis 3:33-39. Soluble VEGF receptors.

Jackson, J., Minton, J., Ho, M., Wei, N. and Winkler J. D. (1997) J. Rheumatol. 24: 1253. Expression of vascular endothelial growth factor in synovial fibroblasts is induced by hypoxia and interleukin 1β.

Keating, M. J., Holmes, R., Lerner, S. and Ho, D. H. (1993) Leuk. Lymphoma 10, 153. L-asparaginase and PEG asparaginase—past, present, and future.

Kendall, R. L. and Thomas, K. A. (1993) Proc. Natl. Acad. Sci. USA 90: 10705-10709. Inhibition of vascular endothelial cell growth factor activity by an endogenously encoded soluble receptor.

Kendall, R. L., Wang, G. and Thomas, K. A. (1996) Biochem. Biophys. Res. Comm. 226: 324-328. Identification of a natural soluble form of the vascular endothelial growth factor receptor, sFlt-1 and its heterodimer with KDR.

Koch, A. Harlow, G. Haines, E. Amento, E. et al., (1994) J. Immunol. 152: 41-49. VEGF: a cytokine modulating endothelial functions in rheumatoid arthritis.

Mahmood, I. (1998) Life Sciences 63: 2365-2371. Interspecies scaling of renally secreted drugs.

Mauceri, H. J., Hanna, N, N., Beckett, M. A., Gorski, D. H., Staba, M-J., Stellato, K. A., Bigelow, K., Heimann, R., Gately, S., Dhanabal, M., Soff, G. A., Sukhatme, V. P., Kufe, D. W. and Weichselbaum, R, R. (1998) Nature 394: 287-291. Combined effects of angiostatin and ionizing radiation in antitumour therapy.

Maini, R. N., Taylor, P. C., Paleolog, E., Charles, P., Ballara, S., Brennan, F. M. and Feldmann M. (1999) Ann Rheum Dis 58(suppl I):I56-I60. Anti-tumour necrosis factor specific antibody (infliximab) treatment provides insights into the pathophysiology of rheumatoid arthritis.

Matsuno, H. Yudoh, K., Uzuli, M. Nakazawa, F., Sawai, T., Ymanaguchi, N. Olsen, B. and Kimura T. (2002) J. Rheumatol. 29: 890-995. Treatment of the angiogenesis inhibitor Flt-1: a novel therapy in rheumatoid arthritis.

Meyers, F. J., Paradise, C., Scudder, S. A., Goodman, G. and Konrad, M. (1991) Clin Pharmacol Ther. 49:307-313. A phase I study including pharmacokinetics of polyethylene glycol conjugated interleukin-2.

Monkarsh, S P, Ma, Y, Aglione, A, Bailon, P, Ciolek, D, DeBarbieri, B, Graves, M C, Hollfelder, K, Michel, H, Palleroni A, Porter, J E, Russoman, E, Roy, S, and Pan Y C. (1997) Anal Biochem. 247(2):434-440. Positional isomers of monopegylated interferon alpha: isolation, characterization, and biological activity.

Mordenti, J., Chen, S. A., Moore, J. A., Ferrailo, B. L. and Green, B. D. (1991) Pharm. Res. 8.1351-1359. Interspecies scaling of clearance and volume of distribution data for five therapeutic proteins.

Molpurgo, M. and Veronese, F. (2004) in Methods in Molecular Biology 283: 45-70. Conjugates of Peptides and Proteins to Polyethylene Glycols.

Nagashima, M. S., Yoshino, T., Ishiwata, T. and Asano, G. (1995) J. Rheumatol. 22: 1624. Role of VEGF in angiogenesis of rheumatoid arthritis.

Oliver S J, Cheng T P, Banquerigo M L, Brahn E. (1998) J Rheumatol, 25:964-969. The effect of thalidomide and 2 analogs on collagen induced arthritis.

Plouët, J. S Sordello, B. Malavaud & N. Ortéga (1996) VEGF and breast cancer. In: Breast cancer. Advances in biology and therapeutics. F. Calvo, M. Crépin, H. Magdalenat, Eds. John Libbey Eurotext: 175-181.

Relf, M., LeJeune, S., Scot, P. et al. (1997) Cancer Res. 57: 963-969. Expression of angiogenic factors in human primary breast cancer.

Restucci, B., De Vico, G and Maiolino, P. (2000) Vet Pathol 37:297-301 Evaluation of Angiogenesis in Canine Mammary Tumors by Quantitative Platelet Endothelial Cell Adhesion Molecule Immunohistochemistry.

Rooney, M., Condell, D. Quinlan, W. Daly, L., Whelan, A. Feighery, C. and Bresnihan, B. (1988) Arthritis Rheum. 31:956-963. Analysis of the histological variation of synovitis in rheumatoid arthritis.

Sato, H. (2002) Adv. Drug Deliv. Rev 54:487-509. Enzymatic procedure for site-specific PEGylation of proteins.

Scharf; S. J. (1990) in "PCR Protocols" (MA Innis, D H Gelfand, J J Sninsky, & T J White, eds.) Academic Press 84-91 Cloning with PCR.

Scola, M. Imagawa, P, Boivin, G., Giannini, E., Glass, D. Hirsh, R., and Grom A. (2001) Arthritis Rheum 44: 794. Expression of angiogenic factors I juvenile rheumatoid arthritis; correlation with revascularization of human synovium engrafted into SCID mice.

Sheffield, W. P. (2001) Current Drug Targets 1:1-10 Modification of Clearance of Therapeutic and Potentially Therapeutic Proteins.

Shibuya, M. (2001) Cell Struct. Funct. (2001) 26(1):25-35. Review. Structure and function of VEGF/VEGF-receptor system involved in angiogenesis.

Shibuya, M., Yamaguchi, S., Yamane, A., Ikeda, T., Tojo, A., Matsushime, H., and Sato, M. (1990) Oncogene 5:519-524. Nucleotide sequence and expression of a novel human receptor-type tyrosine kinase gene (Flt) closely related to the fms family.

Singh, Y., Shikata, N., Kiyozuka, Y., Nambu, H., Morimoto, J., Kurebayashi, J., Hioki, K. and Tsubura, A. (1997) Breast Cancer Res. Treat. 45: 15-27.

Sumariwalla, P. Cao, Y, Wu, H. Feldman, M. and Paleolog, E. (2002) Arthritis Research and Therapy 5:R32-R39. The angiogenesis inhibitor protease-activated kringles 1-5 reduces the severity of murine collagen-induced arthritis.

Takayama, K., Ueno, H., Nakanishe, Y., Sakamoto, T., Inoue, K., Shimizu, K., Oohashi, H., and Hara, N. (2000) Cancer Res. 60: 2169-2177. Suppression of tumor angiogenesis and growth by gene transfer of a soluble form of vascular endothelial growth factor receptor into a remote organ.

Tanaka, K. Yamaguchi, S. Sawano, A. and M. Shibuya (1997) Jpn. J. Cancer Res. 88: 867-876. Characterization of the extracellular domain in vascular endothelial growth factor receptor-1 (Flt-1 tyrosine kinase).

Weber, A., De Bandt, M. and Gundry, M. (2002) J. Rheumatol. 27:2284. Immunohistochemical analysis of vascular endothelial growth factor expression in severe and destructive rheumatoid arthritis.

Weidner, M., Semple, J. P., Welch, W. R., and Folkman, J. (1991) N. Engl. J. Med. 324:1-8. Tumor angiogenesis and metastasis-correlation in invasive breast cancer.

Weismann, C., Fuh, G., Christinger, H. W., Eigenbrot, C., Wells, J. A., and de Vos, A. M. (1997) Cell. 91:695-704. Crystal structure at 1.7 A resolution of VEGF in complex with domain 2 of the sFlt-1 receptor.

Williams R O, Feldmann M, Maini R N (1992) Proc Natl Acad Sci USA 89:9784-9788. Anti-tumor necrosis factor ameliorates joint disease in murine collagen-induced arthritis.

Zalispky, C. (1995) Adv. Drug Delivery Rev 16:157-182.

Zetter B R. (1998) Annual Review of Medicine 49:407-424, Angiogenesis and tumor metastasis.

U.S. Provisional Application Ser. No. 60/723,354, filed Oct. 3, 2005.

Each publication, application or reference cited herein is incorporated herein by reference in its entirety.

While various embodiments of the present invention have been described in detail, it is apparent that modifications and adaptations of those embodiments will occur to those skilled in the art. It is to be expressly understood, however, that such modifications and adaptations are within the scope of the present invention, as set forth above and in the following claims.

What is claimed is:

1. An isolated cysteine variant of sFlt-1 (SEQ ID NO:2) or truncated form thereof consisting of domains 1-3 of sFlt-1, wherein a cysteine residue is substituted for an amino acid selected from the group consisting of G26, D31, N100, N164, N196, N323, and H338; and wherein said variant has in vitro biological activity as measured by the binding of the variant to VEGF.

2. The cysteine variant of claim 1, wherein the substituted cysteine residue is modified by binding with a cysteine-reactive moiety.

3. The cysteine variant of claim 1, wherein the substituted cysteine residue is modified with polyethylene glycol.

4. A composition comprising the variant of claim 1 and a pharmaceutically acceptable carrier.

5. The cysteine variant of claim 1, wherein a cysteine residue is substituted for G26.

6. The cysteine variant of claim 1, wherein a cysteine residue is substituted for D31.

7. The cysteine variant of claim 1, wherein a cysteine residue is substituted for N100.

8. The cysteine variant of claim 1, wherein a cysteine residue is substituted for N164.

9. The cysteine variant of claim 1, wherein a cysteine residue is substituted for N196.

10. The cysteine variant of claim 1, wherein a cysteine residue is substituted for N323.

11. The cysteine variant of claim 1, wherein a cysteine residue is substituted for H338.

* * * * *